US012790387B2

(12) United States Patent
Bazaz et al.

(10) Patent No.: US 12,790,387 B2
(45) Date of Patent: Nov. 10, 2026

(54) METHOD OF PRODUCING ANTIBODIES FROM SINGLE PLASMA CELLS

(71) Applicant: Daro Zist Azma Oxin, Karaj (IR)

(72) Inventors: Zohre Bazaz, Berlin (DE); Masoume Bazaz, Karaj (IR)

(73) Assignee: Daro Zist Azma Oxin, Karaj (IR)

( * ) Notice: Subject to any disclaimer, the term of this patent is extended or adjusted under 35 U.S.C. 154(b) by 390 days.

(21) Appl. No.: 18/505,543

(22) Filed: Nov. 9, 2023

(65) Prior Publication Data

US 2024/0150446 A1 May 9, 2024

Related U.S. Application Data

(63) Continuation-in-part of application No. PCT/IB2022/054328, filed on May 10, 2022.

(60) Provisional application No. 63/186,331, filed on May 10, 2021.

(51) Int. Cl.
*C07K 16/1282* (2026.01)
*C12N 5/0781* (2010.01)
*C12N 5/0786* (2010.01)

(52) U.S. Cl.
CPC ........ *C07K 16/1282* (2013.01); *C12N 5/0635* (2013.01); *C12N 5/0645* (2013.01); *C07K 2317/14* (2013.01); *C07K 2317/21* (2013.01); *C07K 2317/622* (2013.01); *C12N 2500/25* (2013.01); *C12N 2500/30* (2013.01); *C12N 2501/999* (2013.01); *C12N 2502/1358* (2013.01)

(58) Field of Classification Search
None
See application file for complete search history.

(56) References Cited

PUBLICATIONS

Tellier et al., Eur J Immunol. (2019) 49(1):30-37. doi: 10.1002/eji.201847517. Epub Oct. 15, 2018. PMID: 30273443. (Year: 2018).*
Bazzaz, et al. Journal of Isfahan Medical School 32.282 (2014): 534-543. (Year: 2014).*
Tiller, et al. Journal of immunological methods 329.1-2 (2008): 112-124. (Year: 2008).*
Salai, et al. The Journal of Bone & Joint Surgery British vol. 83.6 (2001): 912-915. (Year: 2001).*

* cited by examiner

*Primary Examiner* — Maria Marvich
*Assistant Examiner* — Brendan Thomas Tinsley
(74) *Attorney, Agent, or Firm* — SALIWANCHIK, LLOYD & EISENSCHENK

(57) ABSTRACT

A method for producing an antibody fragment from one or more single plasma cells. The method comprises obtaining a plurality of plasma cells, preparing a plurality of modified cell culture substrates, seeding each respective plasma cell of the plurality of plasma cells on the each respective modified cell culture substrate of the plurality of modified cell culture substrates, forming a plurality of cultured single plasma cells by culturing the seeded each respective plasma cell in a culture medium for a time duration of at least 10 days, and detecting the one or more single plasma cells that secrete the antibody fragment from among the plurality of cultured single plasma cells. The culture medium comprises a conditioned medium harvested from a culture of h-BMSCs, Insulin, Transferrin, Selenium, and Pyruvate.

14 Claims, 9 Drawing Sheets

Specification includes a Sequence Listing.

300

303

400

500

700

800

SEQUENCE LISTING

```
Sequence total quantity: 16
SEQ ID NO: 1           moltype = DNA  length = 21
FEATURE                Location/Qualifiers
source                 1..21
                       mol_type = other DNA
                       organism = synthetic construct
SEQUENCE: 1
naggtgcagc tggtgcagtc t                                            21

SEQ ID NO: 2           moltype = DNA  length = 20
FEATURE                Location/Qualifiers
source                 1..20
                       mol_type = other DNA
                       organism = synthetic construct
SEQUENCE: 2
caggtrcagc tgcagsagtc                                              20

SEQ ID NO: 3           moltype = DNA  length = 21
FEATURE                Location/Qualifiers
source                 1..21
                       mol_type = other DNA
                       organism = synthetic construct
SEQUENCE: 3
gaggtgcagc tgntggagtc t                                            21

SEQ ID NO: 4           moltype = DNA  length = 23
FEATURE                Location/Qualifiers
source                 1..23
                       mol_type = other DNA
                       organism = synthetic construct
```

```
SEQUENCE: 4
gacatcswga tgacccagtc tcc                                          23

SEQ ID NO: 5            moltype = DNA  length = 28
FEATURE                 Location/Qualifiers
source                  1..28
                        mol_type = other DNA
                        organism = synthetic construct
SEQUENCE: 5
gatattgtga tgacycagnc tccactct                                     28

SEQ ID NO: 6            moltype = DNA  length = 23
FEATURE                 Location/Qualifiers
source                  1..23
                        mol_type = other DNA
                        organism = synthetic construct
SEQUENCE: 6
gaaattgtnt gacncagtct cca                                          23

SEQ ID NO: 7            moltype = DNA  length = 21
FEATURE                 Location/Qualifiers
source                  1..21
                        mol_type = other DNA
                        organism = synthetic construct
SEQUENCE: 7
gacsgatggg cccttggtgg a                                            21

SEQ ID NO: 8            moltype = DNA  length = 24
FEATURE                 Location/Qualifiers
source                  1..24
                        mol_type = other DNA
                        organism = synthetic construct
SEQUENCE: 8
gaagacagat ggtgcagcca cagt                                         24

SEQ ID NO: 9            moltype = DNA  length = 36
FEATURE                 Location/Qualifiers
source                  1..36
                        mol_type = other DNA
                        organism = synthetic construct
SEQUENCE: 9
gaataggcca tggcgnaggt gcagctggtg cagtct                            36

SEQ ID NO: 10           moltype = DNA  length = 35
FEATURE                 Location/Qualifiers
source                  1..35
                        mol_type = other DNA
                        organism = synthetic construct
SEQUENCE: 10
gaataggcca tggcgcaggt rcagctgcag sagtc                             35

SEQ ID NO: 11           moltype = DNA  length = 36
FEATURE                 Location/Qualifiers
source                  1..36
                        mol_type = other DNA
                        organism = synthetic construct
SEQUENCE: 11
gaataggcca tggcggaggt gcagctgntg gagtct                            36

SEQ ID NO: 12           moltype = DNA  length = 40
FEATURE                 Location/Qualifiers
source                  1..40
                        mol_type = other DNA
                        organism = synthetic construct
SEQUENCE: 12
tacaggatcc acgcgtagac atcswgatga cccagtctcc                        40

SEQ ID NO: 13           moltype = DNA  length = 41
FEATURE                 Location/Qualifiers
source                  1..41
                        mol_type = other DNA
                        organism = synthetic construct
SEQUENCE: 13
tacaggatcc acgcgtagat attgtgatga cycagactcc a                      41

SEQ ID NO: 14           moltype = DNA  length = 41
FEATURE                 Location/Qualifiers
```

-continued

```
source                  1..41
                        mol_type = other DNA
                        organism = synthetic construct
SEQUENCE: 14
tacaggatcc acgcgtagaa attgtnntga cacagtctcc a                    41

SEQ ID NO: 15           moltype = DNA  length = 26
FEATURE                 Location/Qualifiers
source                  1..26
                        mol_type = other DNA
                        organism = synthetic construct
SEQUENCE: 15
cagtcaagct ttgggccctt ggtgga                                     26

SEQ ID NO: 16           moltype = DNA  length = 42
FEATURE                 Location/Qualifiers
source                  1..42
                        mol_type = other DNA
                        organism = synthetic construct
SEQUENCE: 16
tgacaagctt gcggccgcga agacagatgg tgcagccaca gt                   42
```

METHOD OF PRODUCING ANTIBODIES FROM SINGLE PLASMA CELLS

CROSS-REFERENCE TO RELATED APPLICATION

This application is a continuation-in-part of PCT Application PCT/IB2022/054328, filed on May 10, 2022, entitled "METHOD OF PRODUCING ANTIBODIES FROM SINGLE PLASMA CELLS," which claims the benefit of priority from U.S. Provisional Patent Application Ser. No. 63/186,331, filed on May 10, 2021, entitled "METHOD OF PRODUCING ANTIBODIES FROM PLASMA CELLS" and which are both incorporated herein by reference in their entirety.

REFERENCE TO SEQUENCE LISTING

The Sequence Listing for this application is labeled "HFK.100C1.xml" which was created on Nov. 6, 2023 and is 16,384 bytes. The entire content of the sequence listing is incorporated herein by reference in its entirety.

TECHNICAL FIELD

The present disclosure generally relates to an exemplary method for producing an exemplary antibody fragment from one or more exemplary single plasma cells, and in particular to an exemplary method for culturing exemplary single plasma cells, which may enhance longevity of exemplary plasma cells in vitro.

BACKGROUND

Plasma cells are non-proliferating, terminally-differentiated cells secreting antibodies at very high rate, i.e., about 30 to 50 picograms (pg) per cell per day. Manufacturing of recombinant monoclonal and polyclonal antibodies from plasma cells may be achieved by replicating and expressing immunoglobulin genes within a prokaryotic or eukaryotic host cell. This may be accomplished by: i) utilizing phage display libraries that consist of scrambled immunoglobulin variable heavy (VH) chain genes and immunoglobulin variable light (VL) chain genes isolated from plasma cells, or ii) isolating paired VH and VL genes from individual plasma cells using single cell PCR (polymerase chain reaction). To screen and characterize antibodies secreted by plasma cells, it may be necessary to clone and express immunoglobulin genes in a recombinant form. However, conventional methods for manufacturing antibodies from plasma cells may potentially be time-consuming, challenging, not suited for high-throughput, costly, and inefficient when it comes to obtaining rare antibodies that might be produced by a small fraction of a total plasma cell population.

Creating an appropriate environment to extend the lifespan of plasma cells in vitro, where antibody screening assays (tests measuring antibody-antigen binding) may be effectively monitored, has been a significant challenge. Moreover, it may be beneficial to establish a correlation between results of these screening assays and a specific cell exhibiting optimal expression and/or binding characteristics for a secreted antibody from that particular cell. Thus, there is need for developing efficient methods that may be adapted for high-throughput isolation and screening of antibodies (particularly monoclonal antibodies and recombinant monoclonal antibodies) from plasma cells.

SUMMARY

This summary is intended to provide an overview of the subject matter of the present disclosure, and is not intended to identify essential elements or key elements of the subject matter, nor is it intended to be used to determine the scope of the claimed implementations. Its sole purpose is to present some concepts of one or more aspects in a simplified form as a prelude to the more detailed description that is presented later. The proper scope of the present disclosure may be ascertained from the claims set forth below in view of the detailed description below and the drawings.

One or more exemplary embodiments describe an exemplary method for producing an exemplary antibody fragment from one or more exemplary single plasma cells. In an exemplary embodiment, an exemplary method may comprise obtaining a plurality of exemplary plasma cells and preparing a plurality of exemplary modified cell culture substrates. In an exemplary embodiment, preparing each respective modified cell culture substrate of exemplary plurality of modified cell culture substrates may comprise culturing a plurality of exemplary human bone marrow stomal cells (h-BMSCs) on a respective cell culture substrate of exemplary plurality of cell culture substrates until an exemplary confluency of exemplary plurality of h-BMSCs reaches to at least 70%. In an exemplary embodiment, preparing each respective modified cell culture substrate of exemplary plurality of modified cell culture substrates may include incubating exemplary cultured plurality of h-BMSCs in 2.7-3.3 ng/ml colchicine at an exemplary predetermined temperature level for an exemplary predetermined time duration.

In an exemplary embodiment, an exemplary method may further include seeding each respective plasma cell of exemplary plurality of plasma cells on each respective modified cell culture substrate of exemplary plurality of modified cell culture substrates, and forming exemplary plurality of cultured single plasma cells by culturing an exemplary seeded each respective plasma cell in an exemplary culture medium for an exemplary time duration of at least 10 days. In an exemplary embodiment, an exemplary culture medium may include an exemplary conditioned medium harvested from an exemplary culture of h-BMSCs, Insulin with a concentration of 9.5-10.5 mg/mL, Transferrin with a concentration of 5-6 mg/mL, Selenium with a concentration of 6-7.5 μg/mL, and Pyruvate with a concentration of 0.7-1.3 mM. In an exemplary embodiment, an exemplary method may further include detecting exemplary one or more single plasma cells that may secrete an exemplary antibody fragment from among exemplary plurality of cultured single plasma cells.

This Summary may introduce a number of concepts in a simplified format; the concepts are further disclosed within the "Detailed Description" section. This Summary is not intended to configure essential/key features of the claimed subject matter, nor is intended to limit the scope of the claimed subject matter.

BRIEF DESCRIPTION OF THE DRAWINGS

The novel features which are believed to be characteristic of the present disclosure, as to its structure, organization, use and method of operation, together with further objectives and advantages thereof, will be better understood from the following drawings in which a presently preferred embodiment of the present disclosure will now be illustrated by way of example. It is expressly understood, however, that the drawings are for the purpose of illustration and description only and are not intended as a definition of the limits of the present disclosure. Embodiments of the present disclosure will now be described by way of example in association with the accompanying drawings in which.

BRIEF DESCRIPTION OF THE SEQUENCES

Figure 1A:
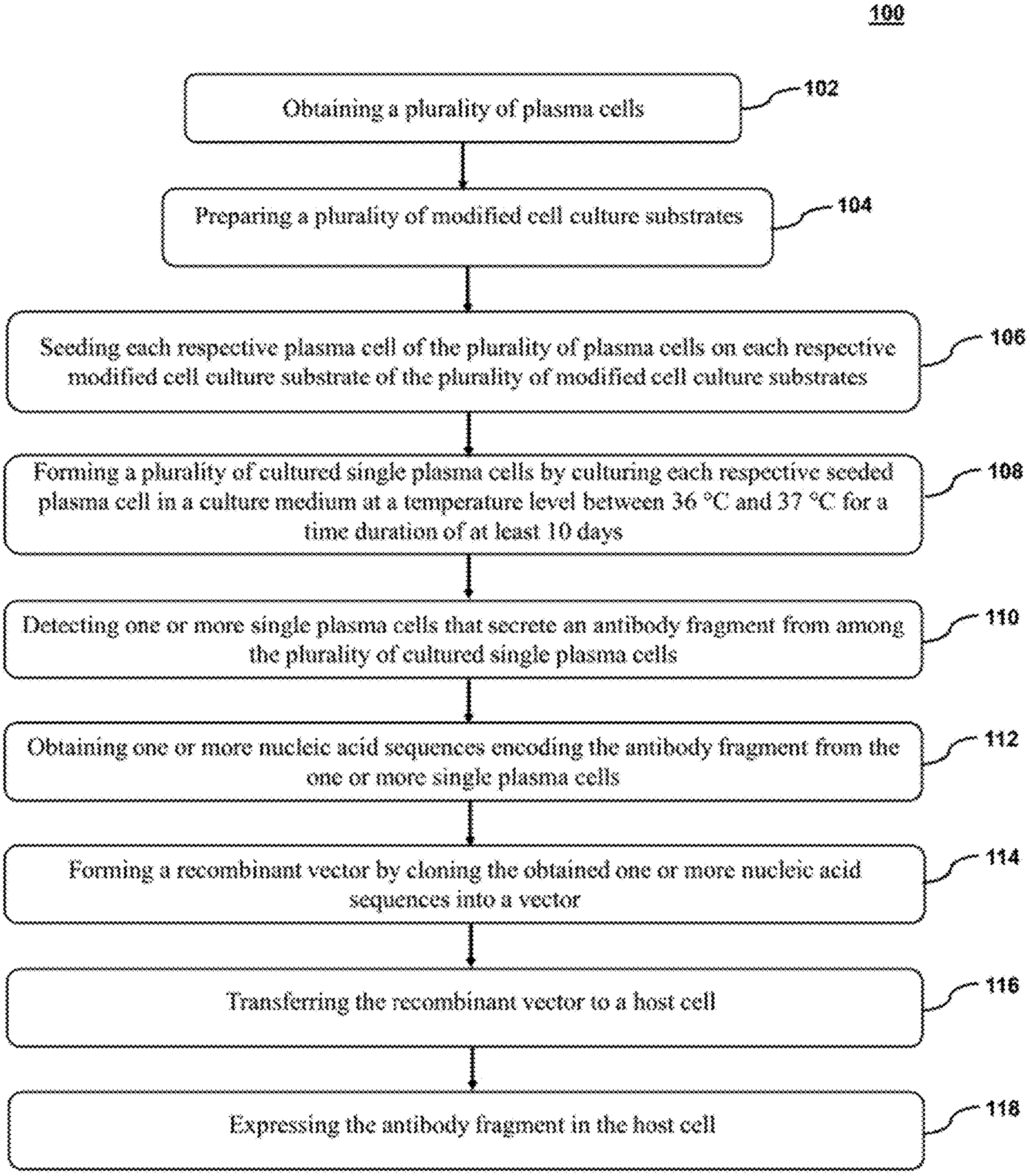
FIG. 1A illustrates a flowchart of an exemplary method for producing an exemplary antibody fragment from one or more exemplary single plasma cells, consistent with one or more exemplary embodiments of the present disclosure.

SEQ ID NO: 1: 1VH1 primer
SEQ ID NO: 2: 1VH2 primer
SEQ ID NO: 3: 1VH3 primer
SEQ ID NO: 4: 1Vk3 primer
SEQ ID NO: 5: 1Vk2 primer
SEQ ID NO: 6: 1Vk3 primer
SEQ ID NO: 7: 1IgG primer
SEQ ID NO: 8: 1Kc primer
SEQ ID NO: 9: 2VH1 primer
SEQ ID NO: 10: 2VH2 primer
SEQ ID NO: 11: 2VH3 primer
SEQ ID NO: 12: 2Vk3 primer
SEQ ID NO: 13: 2Vk2 primer
SEQ ID NO: 14: 2Vk3 primer
SEQ ID NO: 15: 2IgG primer
SEQ ID NO: 16: 2Kc primer

DETAILED DESCRIPTION

In the following detailed description, numerous specific details are set forth by way of examples to provide a thorough understanding of the relevant teachings related to the exemplary embodiments. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in one or more exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be plain to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Provided herein is an exemplary method for producing an exemplary antibody fragment from an exemplary single antibody-expressing cell. An exemplary method may be utilized for producing an exemplary recombinant monoclonal antibody from one or more exemplary single antibody-expressing cells, e.g., single plasma cells. It may be appreciated that exemplary embodiments pertaining to exemplary compositions, exemplary medical treatment methods, exemplary screening methods, exemplary kits, and exemplary catalytic processes related to an exemplary method described in one or more exemplary embodiments may also fall into the context of the present disclosure. In an exemplary embodiment, "antibody-expressing cell(s)" may include, but is not limited to, hybridoma cell, B cell lymphocyte, and plasma cell. B cell lymphocyte may comprise, for example, CD27-positive B cell or CD138-positive B cell. In an exemplary embodiment, B cell may comprise a memory B cell and/or plasma cell. "Antibody" may refer to a full-sized antibody and/or a fragment of a full-sized antibody. A fragment of an antibody may retain antigen-binding activity of a full-sized antibody. In exemplary embodiment, a fragment of an antibody may comprise 10, 20, 30, 40, 50, 60, 70, 80, 90, 100, 150, 200, 300, 400, 500, 600, 700, 800, 900 or 1000 or more consecutive amino acid residues. Antibody fragments may comprise one or more of Fab, Fab', $F(ab')_2$, Fc, Fv, scFv fragments, heavy chain, hinge region, light chain, antigen binding site, and single chain antibodies.

Referring to the figures, FIG. 1A illustrates a flowchart of method 100 for producing an exemplary antibody fragment from one or more exemplary single plasma cells, consistent with one or more exemplary embodiments of the present disclosure. With continued reference to FIG. 1A, in an exemplary embodiment, method 100 may comprise: obtaining a plurality of exemplary plasma cells (step 102); preparing a plurality of exemplary modified cell culture substrates (step 104); seeding each respective plasma cell of exemplary plurality of plasma cells on each respective modified cell culture substrate of exemplary plurality of modified cell culture substrates (step 106); forming a plurality of exemplary cultured single plasma cells by culturing each respective seeded plasma cell in an exemplary culture medium at a temperature level between 36° C. and 37° C. for a time duration of at least 10 days (step 108); detecting one or more exemplary single plasma cells that secrete an exemplary antibody fragment from among exemplary plurality of cultured single plasma cells (step 110); obtaining one or more exemplary nucleic acid sequences encoding an exemplary antibody fragment from one or more exemplary single plasma cells (step 112); forming an exemplary recombinant vector by cloning exemplary obtained one or more nucleic acid sequences into an exemplary vector (step 114); transferring an exemplary recombinant vector to an exemplary host cell (step 116); and expressing an exemplary antibody fragment in an exemplary host cell (step 118).

In further detail with respect to method 100, step 102 may include obtaining a plurality of exemplary plasma cells. "Plasma cell" may refer to a short-lived antibody-expressing cell derived from a type of leukocyte called B cell. In particular, plasma cells may include exemplary differentiated forms of B lymphocytes developed from antigen-activated B lymphocytes in secondary lymphoid organs, such as lymph nodes and spleen, after antigenic stimulation. Plasma cells may be generally characterized by markers including, but not limited to, CD138, CD27, CD9, CD38, CD44, and MHC class II molecules. In an exemplary embodiment, plasma cells may be isolated from various sources, such as bone marrow, peripheral blood, tissues, and bodily fluids, primarily based on their expression of CD138. To enhance isolation process, exemplary surface markers like CD38, CD27, CD44, CD9, and MHC class II molecules may also be utilized in conjunction with CD138. In an exemplary embodiment, obtaining a plurality of exemplary plasma cells may include immunizing an exemplary subject against an exemplary antigen of interest. In an exemplary embodiment, "subject" may refer to an exemplary mammal—such as human, rabbit, rodent (e.g., rat, mouse, hamster, guinea pig, gerbil), ferret, livestock (e.g., goats, horses, pigs, sheep, cows), camel, llama, and monkey—and/or exemplary avian species including, but not limited to, chickens and turkey. In an exemplary embodiment, immunizing an exemplary subject against an exemplary antigen of interest may include immunizing an exemplary subject with an exemplary pathogen containing an exemplary antigen of interest. In an exemplary embodiment, obtaining a plurality of exemplary plasma cells may include obtaining a plurality of exemplary plasma cells from an exemplary subject infected with an exemplary disease (infectious and/or non-infectious) which may be associated with an exemplary antigen of interest. In an exemplary embodiment, obtaining a plurality of exemplary plasma cells may include obtaining a plurality of exemplary plasma cells from an exemplary subject diagnosed with an exemplary autoimmune disease which may be associated with an exemplary antigen of interest.

In an exemplary embodiment, obtaining a plurality of exemplary plasma cells may further include isolating a plurality of exemplary plasma cells from an exemplary sample collected from an exemplary subject's (either immunized or diagnosed with a disease) systemic circulatory system, synovial fluid, cerebrospinal fluid, exudates, bone marrow, and/or different organ tissues. Other exemplary organ tissues containing exemplary plasma cells may include—but not limited to—kidney, bone marrow, lymph nodes, tumor biopsy and a combination thereof. In an exemplary embodiment, isolating a plurality of exemplary plasma cells from an exemplary sample may include isolating a plurality of exemplary plasma cells from an exemplary peripheral blood of an exemplary vaccinated human donor. "Vaccination" may refer to administration of an exemplary antigen capable of inducing an immune response to an exemplary subject, e.g., a human. An exemplary vaccine may include any vaccine known in the art or any available vaccines in the future. For example, in an exemplary embodiment, an exemplary human donor may be vaccinated with an exemplary vaccine comprising—but not limited to—tetanus toxoid, yellow fever, influenza, hepatitis B, tetanus-diphtheria, small pox, COVID-19, cancer vaccines, etc.

In an exemplary embodiment, obtaining a plurality of exemplary plasma cells may further include obtaining a plurality of exemplary plasma cells from an exemplary human donor at least 4 days following an exemplary vaccination. In an exemplary embodiment, In an exemplary embodiment, obtaining a plurality of exemplary plasma cells may further include producing a plurality of exemplary plasma cells in vitro through stimulation of B cells by any exemplary method known in the art, such as antigen-specific and/or polyclonal stimulation of naïve or memory B cells.

Figure 1B:
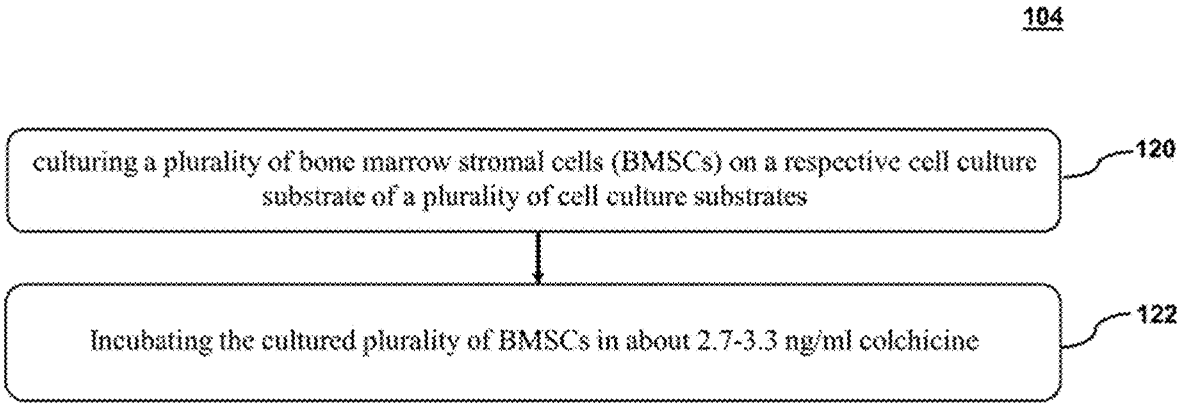
FIG. 1B illustrates an exemplary method for preparing each respective modified cell culture substrate of exemplary plurality of modified cell culture substrates, consistent with one or more exemplary embodiments of the present disclosure.

In further detail with respect to method 100, step 104 may include preparing a plurality of exemplary modified cell culture substrates. In an exemplary embodiment, details of step 104 for preparing each respective modified cell culture substrate of exemplary plurality of modified cell culture substrates are described in context of elements presented in FIG. 1B. FIG. 1B illustrates an exemplary method of step 104 for preparing each respective modified cell culture substrate of exemplary plurality of modified cell culture substrates, consistent with one or more exemplary embodiments of the present disclosure. In further detail with respect to FIG. 1B, an exemplary method of step 104 may include: culturing a plurality of exemplary bone marrow stromal cells (BMSCs) on a respective cell culture substrate of exemplary plurality of cell culture substrates (step 120); and incubating exemplary cultured plurality of BMSCs in about 2.7-3.3 ng/ml colchicine (step 122).

In further detail with respect to FIG. 1B, step 120 may include culturing a plurality of exemplary BMSCs on a respective cell culture substrate of exemplary plurality of cell culture substrates. "Cell culture substrate" may refer to an exemplary material or surface upon which cells are grown in a controlled environment. An exemplary substrate may be designed to support adhesion, growth, and proliferation of cells, while also providing an interface for their interaction with their surroundings. An exemplary cell culture substrate may be composed of various materials such as glass, plastic, gelatinous substances like agar or collagen, or even complex combinations tailored to specific cellular requirements. In an exemplary embodiment, culturing a plurality of exemplary BMSCs on a respective cell culture substrate of exemplary plurality of cell culture substrates may include culturing a plurality of exemplary human BMSCs (h-BMSCs) on a respective cell culture substrate of exemplary plurality of cell culture substrates at an exemplary temperature level between 36° C. and 37° C. (e.g., in an incubator with a temperature of 36-37° C. and 5% $CO_2$) until a confluency of exemplary plurality of h-BMSCs reaches to at least 70%. "Confluency" may refer to the percentage of a surface of a culture substrate that is covered by adherent cells. In an exemplary embodiment, culturing a plurality of exemplary BMSCs on a respective cell culture substrate of exemplary plurality of cell culture substrates may include culturing a plurality of exemplary h-BMSCs in an exemplary general-purpose enriched media (e.g., Roswell Park Memorial Institute Medium (RPMI)) at an exemplary temperature level between about 36° C. and 37° C. until a confluency of exemplary plurality of BMSCs reaches to at least 70%. In an exemplary embodiment, an exemplary general-purpose enriched media may be supplemented with 10-15% (v/v) FBS. In an exemplary embodiment, an exemplary general-purpose enriched media may be further supplemented with L-glutamine and Penicillin/Streptomycin.

"Bone marrow stromal cells" or "BMSCs" may refer to a group of heterogenous and multipotential cells within bone marrow which may act as stem/progenitor cells of a bone tissue and may be indirectly responsible for hematopoiesis. Primary BMSCs may be effectively isolated using an exemplary culture medium and subsequently cultured over several passages. However, passaging process of primary BMSCs may only be sustained for a finite period before exemplary BMSCs enter a phase of senescence. "Passaging" may refer to an exemplary technique that may provide for harvesting cells from a culture and transferring them to one or more vessels containing an exemplary fresh growth medium to keep cells alive and growing for extended periods of time. In an exemplary embodiment, exemplary BMSCs may be selected from exemplary mammalian BMSCs, e.g., human BMSCs.

In an exemplary embodiment, culturing a plurality of exemplary BMSCs on a respective cell culture substrate of exemplary plurality of cell culture substrates may include culturing a plurality of exemplary HS-5 cells on a respective cell culture substrate of a plurality of exemplary cell culture substrates at a temperature level between 36° C. and 37° C. (e.g., in an incubator with a temperature of 36-37° C. and 5% $CO_2$) until a confluency of exemplary plurality of HS-5 cells reaches to at least 70%. In an exemplary embodiment, culturing a plurality of exemplary HS-5 cells on a respective cell culture substrate of a plurality of exemplary cell culture substrates may include culturing exemplary HS-5 cells in an exemplary general-purpose enriched media (e.g., RPMI) at a temperature level between about 36° C. and 37° C. (e.g., in an incubator with a temperature of 36-37° C. and 5% $CO_2$) until a confluency of exemplary plurality of HS-5 cells reaches to at least 70%. "HS-5 cells" may refer to an exemplary human marrow stromal cell line (i.e., adherent fibroblast-like cell line) immortalized by transduction with exemplary human papilloma virus E6/E7 genes. In an exemplary embodiment, exemplary HS-5 cells may secrete significant levels of granulocyte-macrophage colony stimulating factor (GM-CSF), granulocyte-CSF (G-CSF), macrophage-CSF (M-CSF), macrophage-inhibitory protein-1 alpha, Kit ligand (KL), interleukin-1 alpha (IL-1alpha), IL-1RA, IL-8, IL-1beta, IL-6, IL-11, and leukemia inhibitory factor (LIF).

In further detail with respect to FIG. 1B, step 122 may include incubating exemplary cultured plurality of BMSCs in about 2.7-3.3 ng/ml colchicine. In an exemplary embodiment, incubating exemplary cultured plurality of BMSCs in about 2.7-3.3 ng/ml colchicine may include incubating exemplary cultured plurality of HS-5 cells in about 3 ng/ml colchicine at an exemplary temperature level between about 36° C. and 37° C. for a time duration between about 18 and 24 hours using an exemplary incubator with a temperature of 36-37° C. and 5% $CO_2$. Colchicine ($C_{22}H_{25}NO_6$) and its derivatives may be a group of chemicals capable of inhibiting mitosis by disrupting microtubules and inhibiting tubulin polymerization. In an exemplary embodiment, incubating exemplary cultured plurality of BMSCs in about 3 ng/ml colchicine at an exemplary temperature level between 36° C. and 37° C. for a time duration between 18 and 24 hours may include incubating exemplary cultured plurality of HS-5 cells in about 3 ng/ml colchicine at an exemplary temperature level between about 36° C. and 37° C. for a time duration between about 18 and 24 hours to arrest or reduce cell growth and/or proliferation, and in turn produce a plurality of non-dividing HS-5 cells.

In further detail with respect to method 100, step 106 may include seeding each respective plasma cell of exemplary plurality of plasma cells on each respective modified cell culture substrate of exemplary plurality of modified cell culture substrates. "Cell seeding" may refer to uniformly spreading cells to a culture vessel to form a monolayer. In an exemplary embodiment, each respective modified cell culture substrate may comprise a plurality of exemplary non-dividing BMSCs with an exemplary confluency of at least 70%. In an exemplary embodiment, each respective modified cell culture substrate may comprise a plurality of exemplary non-dividing HS-5 cells with an exemplary confluency between about 70% and 90%. In particular, in an exemplary embodiment, seeding each respective plasma cell of exemplary plurality of plasma cells on each respective modified cell culture substrate may include seeding each respective plasma cell of exemplary plurality of plasma cells on the top of non-dividing BMSCs adhered to each respective cell culture substrate. In an exemplary embodiment, seeding each respective plasma cell of exemplary plurality of plasma cells on each respective modified cell culture substrate may include seeding each respective plasma cell of exemplary plurality of plasma cells on the top of exemplary non-dividing HS-5 cells adhered to each respective cell culture substrate.

In an exemplary embodiment, seeding each respective plasma cell of exemplary plurality of plasma cells on each respective modified cell culture substrate of exemplary plurality of modified cell culture substrates may include isolating/sorting exemplary plurality of plasma cells in form of single plasma cells using one or more exemplary techniques. In one or more exemplary embodiments, exemplary techniques for isolating/sorting exemplary plurality of plasma cells in form of single plasma cells may include, but are not limited to, immunomagnetic cell separation, fluorescence-activated cell sorting (FACS), density gradient centrifugation, immunodensity cell separation, sedimentation, adhesion, microfluidic cell separation, aptamer technology, Buoyancy-activated cell sorting (BACS), laser capture microdissection (LCM), Laser capture microdissection (LCM), immunoguided laser capture microdissection, limiting dilution, micromanipulation, etc. In an exemplary embodiment, isolating/sorting exemplary plurality of plasma cells in form of single plasma cells may include using an exemplary FACS technique to isolate single plasma cells from other peripheral blood mononuclear cells (PBMCs) and deposit each respective plasma cell on each respective modified cell culture substrate of exemplary plurality of modified cell culture substrates.

In an exemplary embodiment, an exemplary antibody fragment (e.g., a monoclonal antibody) may be obtained from a low concentration, i.e., a small number, of plasma cells per culture. An exemplary small number of plasma cells per culture may include about 1 to about 10, about 1 to about 15, about 1 to about 20, about 1 to about 25, about 1 to about 30, about 1 to about 40, about 1 to about 50, about 1 to about 60, about 1 to about 70, about 1 to about 80, about 1 to about 90, and about 1 to about 100 plasma cells per culture. Due to the fact that an exemplary monoclonal antibody or an exemplary fragment thereof may be produced by an exemplary single plasma cell, culturing exemplary single plasma cells in separate cultures may lead to production of an exemplary monoclonal antibody. Thereby, in an exemplary embodiment, exemplary plasma cells may be ideally isolated in form of single plasma cells and each of them may be deposited/seeded in a separate modified cell culture substrate (i.e., 1 plasma cell per each culture). For example, a microtiter plate, such as a 96-well, a 384-well, or a 1536-well plate, may be used for providing separate culturing areas or modified cell culture substrates for each of exemplary isolated single plasma cells. Thus, in an exemplary embodiment, each respective well of an exemplary multi-well plate may ideally contain an exemplary single plasma cell.

In further detail with respect to method 100, step 108 may include forming a plurality of exemplary cultured single plasma cells by culturing each respective seeded plasma cell in an exemplary culture medium at a temperature level between 36° C. and 37° C. for a time duration of at least 10 days. In an exemplary embodiment, culturing each respective seeded plasma cell in an exemplary culture medium at a temperature level between 36° C. and 37° C. for a time duration of at least 10 days may include culturing each respective seeded plasma cell in an exemplary culture medium at a temperature level between about 36° C. and 37° C. (e.g., in an incubator with a temperature of 36-37° C. and 5% $CO_2$) for a time duration of at least 10 days. In an exemplary embodiment, an exemplary culture medium may include an exemplary conditioned medium harvested from an exemplary culture of BMSCs or h-BMSCs. In an exemplary embodiment, an exemplary culture medium may include an exemplary conditioned medium harvested from an exemplary culture of HS-5 cells. “Conditioned medium” may refer to an exemplary medium that has been utilized to grow cells and has thus been altered or conditioned by exemplary cells. During growth phase, cells may have secreted certain substances into an exemplary cell culture medium such as growth factors, cytokines, extracellular matrix proteins, nutrients, metabolites, and/or factors (e.g., cell death-stable proteins), and other biomolecules.

In an exemplary embodiment, an exemplary conditioned medium of step 108 may comprise an exemplary secretome of exemplary cultured BMSCs and/or exemplary HS-5 cells. In an exemplary embodiment, an exemplary conditioned medium used in step 108 may include an exemplary general-purpose enriched media, such as RPMI medium, which may have been used for culturing exemplary BMSCs and/or exemplary HS-5 cells and, subsequently, harvested from an exemplary culture of BMSCs and/or exemplary HS-5 cells.

In an exemplary embodiment, an exemplary conditioned medium may comprise granulocyte-macrophage colony stimulating factor (GM-CSF), granulocyte-CSF (G-CSF), macrophage-CSF (M-CSF), macrophage-inhibitory protein-1 alpha, Kit ligand (KL), interleukin-1 alpha (IL-1alpha), IL-1RA, IL-8, IL-1beta, IL-6, IL-11, and leukemia inhibitory factor (LIF).

In an exemplary embodiment, culturing each respective seeded plasma cell in an exemplary culture medium at a temperature level between about 36° C. and 37° C. for a time duration of at least 10 days may include culturing each respective seeded plasma cell in an exemplary culture medium comprising an exemplary conditioned medium (e.g., 20-50 μL), Insulin with a concentration of about 9.5-10.5 mg/mL, Transferrin with a concentration of about 5-6 mg/mL, Selenium with a concentration of about 6-7.5 μg/mL, and Pyruvate with a concentration of about 0.7-1.3 mM. In an exemplary embodiment, culturing each respective seeded plasma cell in an exemplary culture medium at a temperature level between about 36° C. and 37° C. for a time duration of at least 10 days may include culturing each respective seeded plasma cell in an exemplary culture medium comprising an exemplary conditioned medium (e.g., 20-50 μL), Insulin with a concentration of about 10 mg/mL, Transferrin with a concentration of about 5.5 mg/mL, Selenium with a concentration of about 6.8 μg/mL, and Pyruvate with a concentration of about 1 mM. In an exemplary embodiment, culturing each respective seeded plasma cell in an exemplary culture medium may include: adding an exemplary culture medium to each respective modified cell culture substrate containing a respective single plasma cell; and culturing each respective seeded plasma cell in an exemplary culture medium at a temperature level between about 36° C. and 37° C. for a time duration of at least 10 days during which an exemplary culture medium may be refreshed every 1 day or less, every 2 days or less, every 3 days or less, every 4 days or less, every 5 days or less, and more. In an exemplary embodiment, an exemplary culture medium of step 108 may prolong survival of exemplary single plasma cells to at least 5 days, at least 10 days, at least 20 days, and at least 30 days. It may be understood that unlike memory B cells, which may be induced to expand into clones of antibody-expressing cells through immortalization, plasma cells are not capable of division, stimulation, or immortalization. “Clone” may refer to a group of identical cells sharing a common ancestry, i.e., may be derived from a same cell.

While plasma cells have the potential to survive for extended durations in vivo, their survival may not exceed 24 hours under laboratory conditions (in vitro). Consequently, to utilize these plasma cells for antibody production, it may be necessary to provide an ideal culture environment that may sustain their viability and preserve their capacity to produce antibodies. Plasma cells are known to continuously secrete antibodies; hence, enhancing survival of plasma cells may boost the quantity of antibodies released over time. In an exemplary embodiment, steps 104-108 of method 100 may extend the lifespan of plasma cells in vitro allowing for production of exemplary antibodies or antibody fragments in quantities sufficient for their characterization. In an exemplary embodiment, step 108 may result in antibody production at concentrations that are beneficial for conducting various screening assays, including, but not limited to, neutralization assays, binding assays, and any other assay that may determine functionality and other characteristics of exemplary secreted antibodies. In an exemplary embodiment, steps 104-108 of method 100 may extend lifespan of exemplary plasma cells in vitro, either for a short-term (e.g., a minimum of 2 days) or a long-term duration (e.g., at least 10 days).

In further detail with respect to method 100, step 110 may include detecting one or more exemplary single plasma cells that may secrete an exemplary antibody fragment from among exemplary plurality of cultured plasma cells. In an exemplary embodiment, detecting one or more exemplary single plasma cells that may secrete an exemplary antibody fragment from among exemplary plurality of cultured plasma cells may include detecting one or more exemplary single plasma cells secreting an exemplary antibody fragment from among exemplary plurality of cultured plasma cells using an exemplary screening assay. In an exemplary embodiment, detecting one or more exemplary single plasma cells secreting an exemplary antibody fragment from among exemplary plurality of cultured plasma cells using an exemplary screening assay may include screening binding of an exemplary antibody expressed by each respective cultured plasma cell to an exemplary antigen of interest with the aim of identifying one or more exemplary plasma cells secreting specific/monoclonal antibodies (i.e., exemplary antibodies binding to a specific antigen or a specific epitope). In an exemplary embodiment, detecting one or more exemplary single plasma cells secreting an exemplary antibody fragment from among exemplary plurality of cultured plasma cells using an exemplary screening assay may include performing one or more exemplary enzyme-linked immunosorbent assays (ELISA).

In further detail with respect to method 100, step 112 may include obtaining one or more exemplary nucleic acid sequences encoding an exemplary antibody fragment from one or more exemplary single plasma cells. In an exemplary embodiment, obtaining one or more exemplary nucleic acid sequences encoding an exemplary antibody fragment from one or more exemplary single plasma cells may include obtaining one or more exemplary nucleic acid sequences including messenger Ribonucleic Acid (mRNA) and/or complementary Deoxyribonucleic Acid (cDNA). In an exemplary embodiment, exemplary antibody fragments may comprise one or more of Fab, Fab', $F(ab')_2$, Fc, Fv, scFv fragments, heavy chain, hinge region, light chain, antigen binding site, and single chain antibodies. In an exemplary embodiment, an exemplary antibody fragment may include—but is not limited to—an exemplary Variable Light (VL) chain and/or an exemplary Variable Heavy (VH) chain of an exemplary antibody. "Variable region" or "variable domain" may refer to a portion of light and/or heavy chains of an antibody, typically including approximately an amino-terminal 120 to 130 amino acids in a heavy chain and about 100 to 110 amino-terminal amino acids in a light chain. Variable regions typically differ extensively in amino acid sequence even among antibodies of the same species. Variable region of an antibody may typically determine binding and specificity of each particular antibody to its target antigen. Variability in sequence is concentrated in those regions referred to as complementarity-determining regions (CDRs). On the other hand, highly conserved regions in variable domain are called framework regions (FR). CDRs may comprise amino acids which are largely responsible for direct interaction of an antibody with a target antigen, however, amino acids of FRs may significantly affect antigen binding/recognition. "Light chain," when used in reference to an antibody, may refer to two distinct types of kappa (κ) or lambda (l) chains based on an amino acid sequence of constant domains. "Heavy chain," when used in reference to an antibody, may refer to five distinct types of alpha, delta, epsilon, gamma and mu, based on the amino acid sequence of heavy chain constant domain. Combination of heavy and light chains may give rise to five known classes of antibodies: IgA, IgD, IgE, IgG and IgM, respectively, including four known subclasses of IgG, designated as IgG1, IgG2, IgG3 and IgG4.

Figure 1C:
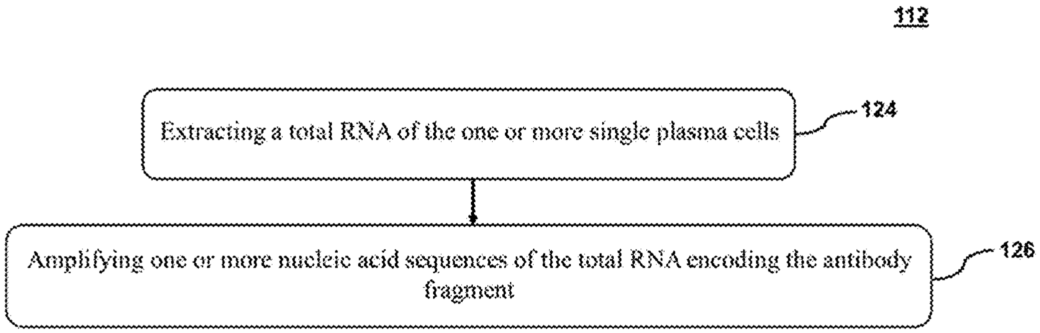
FIG. 1C illustrates an exemplary method for obtaining one or more exemplary nucleic acid sequences encoding an exemplary antibody fragment from one or more exemplary single plasma cells, consistent with one or more exemplary embodiments of the present disclosure.

In an exemplary embodiment, details of step 112 for obtaining one or more exemplary nucleic acid sequences encoding an exemplary antibody fragment from one or more exemplary single plasma cells are described in context of elements presented in FIG. 1C. FIG. 1C illustrates an exemplary method of step 112 for obtaining one or more exemplary nucleic acid sequences encoding an exemplary antibody fragment from one or more exemplary single plasma cells, consistent with one or more exemplary embodiments of the present disclosure. In further detail with respect to FIG. 1C, an exemplary method of step 112 may include: extracting an exemplary total RNA of one or more exemplary single plasma cells (step 124); and amplifying one or more exemplary nucleic acid sequences of an exemplary total RNA encoding an exemplary antibody fragment (step 126).

In further detail with respect to FIG. 1C, step 124 may include extracting an exemplary total RNA of one or more exemplary single plasma cells. In an exemplary embodiment, extracting an exemplary total RNA of one or more exemplary single plasma cells may include extracting an exemplary total RNA of one or more exemplary single plasma cells by lysing one or more exemplary single plasma cells. In an exemplary embodiment, extracting an exemplary total RNA of one or more exemplary single plasma cells may include extracting an exemplary total RNA using an exemplary method including—but not limited to—organic extraction (e.g., phenol-Guanidine Isothiocyanate (GITC)-based solutions), paramagnetic particle technology, and silica-membrane based spin column technology.

In further detail with respect to FIG. 1C, step 126 may include amplifying one or more exemplary nucleic acid sequences of an exemplary total RNA encoding an exemplary antibody fragment. In an exemplary embodiment, amplifying one or more exemplary nucleic acid sequences of an exemplary total RNA encoding an exemplary antibody fragment may include amplifying mRNA and/or cDNA of an exemplary total RNA encoding an exemplary antibody fragment. In an exemplary embodiment, amplifying mRNA and/or cDNA of an exemplary total RNA encoding an exemplary antibody fragment may include amplifying mRNA and/or cDNA of an exemplary total RNA encoding an exemplary antibody fragment by Polymerase Chain Reaction (PCR). In an exemplary embodiment, an exemplary method of step 112 may further include sequencing one or more exemplary amplified nucleic acid sequences prior to their utilization for expression of an exemplary fragment of an exemplary antibody. It may be understood that nucleic acid sequencing may be accomplished using an exemplary automated sequencing method.

with further reference to FIG. 1A and in further detail with respect to step 114, step 114 may include forming an exemplary recombinant vector by cloning exemplary extracted one or more nucleic acid sequences into an exemplary vector. In an exemplary embodiment, an exemplary recombinant vector may harbor an exemplary amplified nucleic acid sequence. "Vector" may refer to a DNA molecule used as a vehicle to artificially carry foreign genetic material into another cell, where it may be replicated and/or expressed. An exemplary vector may include a replicon, such as a plasmid, phage, or cosmid, into which another DNA segment may be inserted so as to bring about replication of an exemplary inserted segment. An exemplary vector may include a broad array of nucleic acid molecules including, but not limited to, single-stranded, double-stranded, or partially double-stranded. In an exemplary embodiment, an exemplary vector may consist of one or more free ends, or even no free ends at all, as seen in circular vectors. Furthermore, an exemplary vector may be composed of DNA, RNA or a combination of both. "Plasmid," a type of vector, may refer to a circular double stranded DNA loop into which additional DNA segments may be inserted, such as by standard molecular cloning techniques. Another variety of vector may include viral vector, where DNA or RNA sequences derived from viruses are incorporated into a vector for packaging into a virus, such as retroviruses, replication-deficient retroviruses, adenoviruses, replication-deficient adenoviruses, and adeno-associated viruses. Exemplary viral vectors may embody polynucleotides transported by a virus for introduction into a host cell. Certain exemplary vectors may have an ability to replicate independently within a host cell they are introduced into; for example, bacterial vectors possessing a bacterial origin of replication and episomal mammalian vectors. Conversely, other exemplary vectors, such as non-episomal mammalian vectors, may integrate themselves into an a genome of a host cell upon their introduction. As a result, non-episomal vectors may replicate in conjunction with a host genome.

Furthermore, exemplary expression vectors may guide expression of genes to which they are operatively linked. Frequently used expression vectors in recombinant DNA methodologies may be typically in form of plasmids. Recombinant expression vectors may comprise a polynucleotide or nucleic acid molecule in a format conducive to expression of a nucleic acid within a host cell. In an exemplary embodiment, recombinant expression vectors may contain one or more exemplary regulatory elements. Selection of regulatory elements may be influenced by exemplary chosen host cells. Exemplary regulatory elements may be operatively linked to an exemplary nucleic acid sequence that is expressing. Being "operatively linked" may imply that a nucleotide sequence of interest is linked to exemplary regulatory element(s) in such a way that it enables expression of nucleotide sequence. In certain exemplary instances, a vector may also include regulatory elements that control expression of a polypeptide.

In an exemplary embodiment, selection of a vector might be contingent upon a host cell or organism it is intended to transform. For instance, a vector may be an autonomously replicating one—in other words, a vector may exist as an extra-chromosomal entity with its replication process being independent of chromosomal replication (for example, a plasmid). On the other hand, a vector may be designed such that upon transformation into a host cell or organism, it may integrate partially or wholly into a genome of a host cell or organism and replicate alongside chromosomes it has integrated into.

In further detail with respect to method 100, step 116 may include transferring an exemplary recombinant vector to an exemplary host cell. "Transferring" may refer to a process of introducing a fragment of nucleic acid into a host organism or cell. In an exemplary embodiment, transferring may occur either via a plasmid or through stable integration into a host organism's chromosome, leading to genetically stable inheritance. "Host cell/organism" may refer to a cell with a potential to be transformed by an exogenous DNA sequence. In an exemplary embodiment, an exemplary host cell/organism may include, but is not limited to, prokaryotic cells like *E. coli*, as well as eukaryotic cells. Examples of eukaryotic cells include yeast cells, insect cells, plant cells, and animal cells. Exemplary animal host cells may comprise mammalian cells such as mice cells, human cells, etc.

In an exemplary embodiment, an exemplary process of transferring a vector into a host cell or organism may include any method that allows for the transfer of nucleic acids into a host cell or organism. In an exemplary embodiment, transferring an exemplary vector may be carried out using a standard technique, which may be chosen based on a specific type of host cell or organism involved. In an exemplary embodiment, methods of vector transfer may include, but are not limited to, electroporation, protoplast fusion, calcium phosphate ($CaPO_4$) precipitation, calcium chloride ($CaCl_2$) precipitation, agitation with silicon carbide fiber, and transformation mediated by *agrobacterium*, PEG, dextran sulfate, lipofectamine, and desiccation/inhibition-mediated transformation.

In further detail with respect to method 100, step 118 may include expressing an exemplary antibody fragment in an exemplary host cell. "Expression" may refer to creation of an RNA replica from a nucleic acid sequence, a process often referred to as 'transcription'. Expression may further include conversion of information conveyed by nucleic acid sequences into amino acid sequences, a process recognized as 'translation'. In other words, protein expression may entail both gene expression and protein synthesis. In an exemplary embodiment, an exemplary antibody fragment may be produced using an exemplary virus or vector transformed into a eukaryotic cell. An exemplary eukaryotic cell may be a CHO, 293F, 293T, or yeast cell. In an exemplary embodiment, an exemplary antibody fragment may be produced using an exemplary vector or phage transformed into a prokaryotic cell. An exemplary prokaryotic cell may include a bacterial cell such as *E. coli*. Furthermore, in an exemplary embodiment, an exemplary antibody fragment may be expressed using a system that is free of cells.

In an exemplary embodiment, an exemplary antibody fragment may be isolated from an exemplary culture supernatant through centrifugation or affinity chromatography. In an exemplary embodiment, an exemplary antibody fragment may be isolated based on its binding specificity. As an example, an exemplary antibody fragment may be isolated by introducing it to an exemplary solid support containing an exemplary immobilized antigen that binds specifically to an exemplary antibody fragment.

In an exemplary embodiment, step 118 may further include isolating an exemplary antibody fragment using one or more exemplary anti-IgG, -IgA, -IgE, -IgD, or -IgM antibodies. In an exemplary embodiment, to isolate an exemplary antibody fragment, one or more of exemplary anti-IgG, -IgA, -IgE, -IgD, or -IgM antibodies may be immobilized to an exemplary solid support. In an exemplary embodiment, one or more exemplary isolation and purification techniques may be employed, including but not limited to ultracentrifugation, precipitation and differential solubilization, chromatography, and gradient centrifugation. Furthermore, in an exemplary embodiment, step 118 may further include removing reductants from an exemplary antibody fragment using an exemplary method including, but not limited to, ultrafiltration, dialysis, and chromatography.

In an exemplary embodiment, step 118 may further include characterizing an exemplary antibody fragment. In an exemplary embodiment, characterizing an exemplary antibody fragment may include measuring binding specificity of an exemplary antibody fragment, and identifying an exemplary specific epitope that an exemplary antibody fragment recognizes. It may be appreciated that exemplary plasma cells isolated from peripheral blood of an exemplary human donor, who has been immunized against an exemplary antigen or pathogen, may be capable of producing exemplary antibodies or antibody fragments which may bind specifically to that antigen or pathogen. In an exemplary embodiment, characterizing an exemplary antibody fragment may include characterizing an exemplary antibody fragment through protein sequencing with exemplary methods known in the art including, but not limited to, mass spectrometry, Edman degradation, and next generation protein sequencing.

It may be understood that method 100 may be used for producing exemplary antibodies or antibody fragments of any isotype including IgG, IgM, IgD, and IgD. Meanwhile, it is to be understood that in one or more exemplary embodiments, exemplary amino acid sequences may be prepared by in vitro transcription/translation or recombinantly. Exemplary amino acid sequences may also be obtained synthetically, e.g., using a commercially available peptide synthesizer. Exemplary methods of synthetic peptide synthesis may include, but are not limited to, solid-phase peptide synthesis, liquid-phase peptide synthesis, etc.

Exemplary nucleic acid molecules/sequences described above may be non-naturally occurring. One or more exemplary embodiments may provide exemplary nucleic acid molecules in synthetic, recombinant, isolated, and/or purified form. Synthetic may refer to exemplary polynucleotides prepared, produced, and/or manufactured by the hand of man. Synthesis of exemplary polynucleotides may be enzymatic or chemical.

EXAMPLES

Hereinafter, the present disclosure will be described in further detail with reference to examples. It will be obvious to a person having ordinary skill in the art that these examples may be for illustrative purposes only and are not to be interpreted to limit the scope of the present disclosure.

Example 1: Immunization of a Healthy Adult Donor Against Tetanus Toxoid

In this example, a healthy adult human donor with a sufficient serum antibody titer against tetanus toxoid was selected and received a boost vaccination. The donor's antibody titer was assessed before and after receiving a boost vaccination by enzyme-linked immunosorbent assay (ELISA). ELISA test results indicated a significant increase in an exemplary concentration of anti-tetanus immunoglobulin G (IgG) in an exemplary donor's serum after vaccination. Based on an exemplary standard calibration curve for tetanus antitoxin, the concentration of anti-tetanus antibody before and after vaccination was measured to be 0.5 and 16 IU/ml, respectively. These results may demonstrate a sufficient humoral immune response against tetanus vaccine after boosting.

Example 2: Obtaining Single Plasma Cells

In this example, single plasma cells were sorted from peripheral blood mononuclear cells (PBMCs). For this purpose, PBMCs were isolated from a fresh peripheral blood collected from an exemplary immunized donor (in Example 1) by Ficoll® density gradient centrifugation. Next, single plasma cells were sorted from PBMCs by fluorescent activated cell sorting (FACS) technique. To perform FACS, exemplary isolated PBMCs were stained using fluorescent anti-human plasma cell marker antibodies. Thus, fluorescent-conjugated monoclonal antibodies (mAbs) against human plasma cells were added to a suspension of PBMCs and incubated for 30 min in dark at 4° C. The stained cells were washed twice with PBS (phosphate-buffered saline) buffer, collected by centrifugation at 1500 rpm for 5 min, and finally suspended in complete RPMI (Roswell Park Memorial Institute) medium—i.e., RPMI medium that may be supplemented with 2 mM L-Glutamine and 10% FBS. At the end, single plasma cells were FACS-sorted and analyzed using FACSAria™ II system (BD bioscience).

Figure 2:
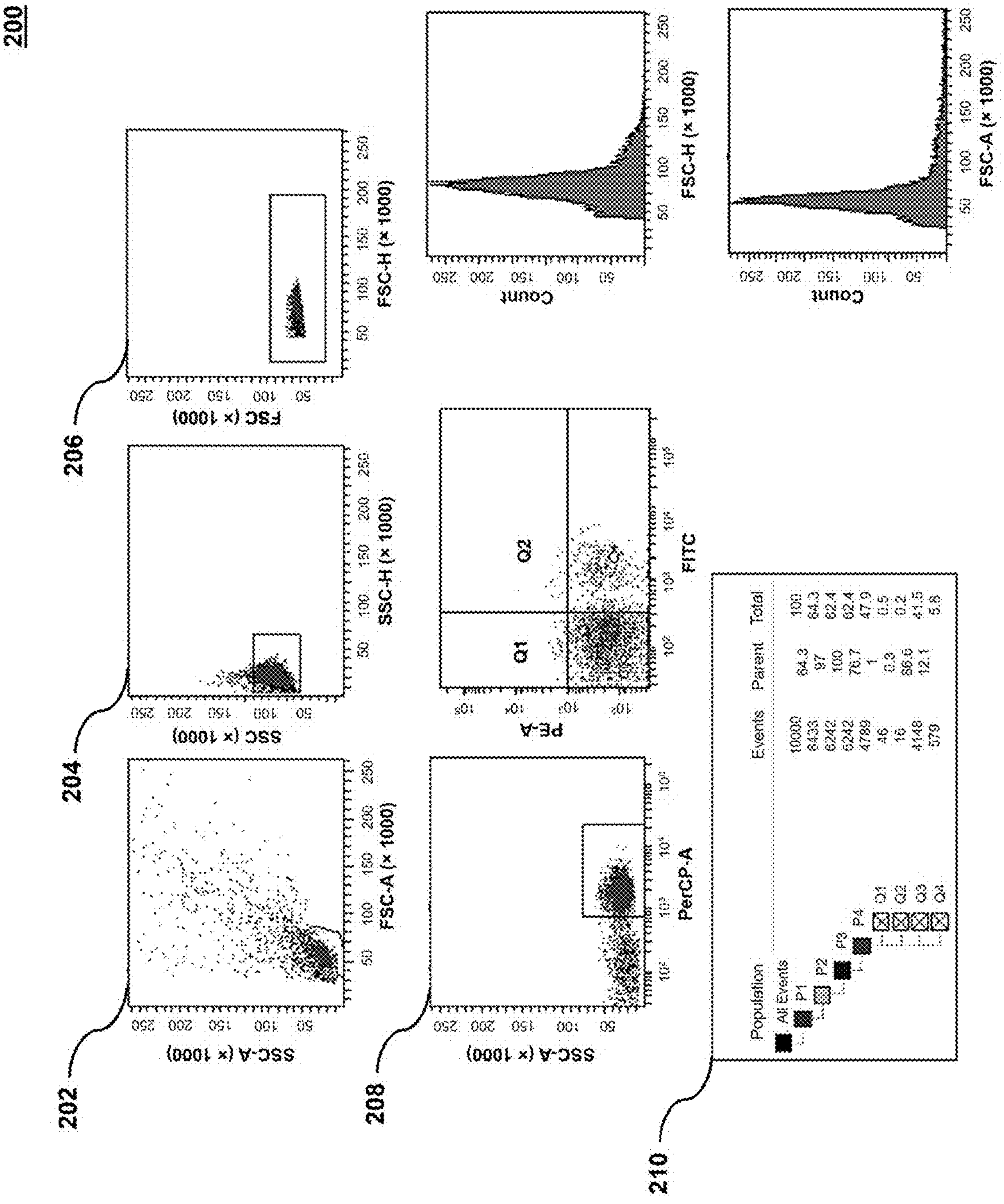
FIG. 2 illustrates exemplary graphs representing flow cytometry analysis of exemplary peripheral blood mononuclear cells (PBMCs) isolated from an exemplary donor's peripheral blood before and after boost vaccination, consistent with one or more exemplary embodiments of the present disclosure.

FIG. 2 illustrates graphs 200 representing flow cytometry analysis of exemplary PBMCs isolated from an exemplary donor's peripheral blood before and after boost vaccination, consistent with one or more exemplary embodiments of the present disclosure. In further detail with respect to graphs 200, plasma cells may constitute 0.03% of an exemplary donor's PBMCs before vaccination. However, following vaccination, an exemplary percentage of plasma cells may raise up to 0.3%. In further detail with respect to graphs 202, 204, and 206, single lymphocytes may be identified by observing forward scatter (FSC) and side scatter (SSC) parameters (illustrated as P1, P2 and P3 gated cells in graphs 202, 204, and 206). In addition, as illustrated in graph 208, CD45-positive PBMCs were identified and gated as P4; CD45-positive PBMCs expressing both CD38 and CD19 markers (shown as gate Q2 in graph 210) were identified as single plasma cells that may constitute about 0.3% of exemplary isolated PBMCs. Exemplary results obtained in Example 2 may demonstrate that the number of plasma cells may increase in an exemplary donor's peripheral blood about 7 days after vaccination. With further reference to graphs 200, exemplary gated plasma cells (i.e., gate Q2) were FACS-sorted to yield a single plasma cell per each well in a microtiter plate.

Example 3: Culturing Single Plasma Cells

In this example, an exemplary method was developed to maintain exemplary sorted single plasma cells (that are normally short-lived) alive and active such that plasma cells are capable of producing antibody for at least 10 days. For this purpose, human bone marrow stromal cells (hBMSCs) were selected as feeder cells to be co-cultured with exemplary single plasma cells in each well. In an exemplary embodiment, HS-5 cells were selected as feeder cells to be co-cultured with exemplary single plasma cells in each respective well. hBMSCs/HS-5 cells were seeded in each respective well of a 96-well plate and cultured (in a medium comprising complete RPMI supplemented with penicillin/streptomycin) at 37° C. with 5% $CO_2$ until reaching a 70 to 90% confluency. An exemplary surrounding medium of an exemplary cultured hBMSCs/HS-5 cells was separated during their culture and stored at −70° C. to further be used as conditioned medium in the next steps. "Conditioned medium" may refer to a spent medium that may be harvested from an exemplary culture of hBMSCs/HS-5 cells. In an exemplary embodiment, when the hBMSCs/HS-5 cells reach a confluency of about 70% and more, colchicine may be added (up to 3 ng/ml) to each respective well. Exemplary cultured hBMSCs/HS-5 cells were incubated with colchicine for 18 to 24 h (at 37° C. with 5% $CO_2$).

Then, an exemplary culture medium surrounding exemplary cultured hBMSCs/HS-5 cells was removed from each respective well and an exemplary single plasma cell (isolated from an exemplary immunized donor's PBMCs) was seeded—using FACS technique—in each respective well of an exemplary 96-well plate that were pre-seeded with exemplary hBMSCs/HS-5 cells. Exemplary single plasma cells were maintained for at least 10 days in an exemplary cocktail comprising complete RPMI supplemented with an exemplary conditioned medium, Insulin (10 mg/ml), Transferrin (5.5 mg/ml), Selenium (6.8 μg/ml), and Pyruvate (1 mM). In an exemplary embodiment, complete RPMI may refer to an exemplary RPMI medium supplemented with 2 mM L-Glutamine and 10% FBS. In an exemplary embodiment, an exemplary complete RPMI may further comprise penicillin/streptomycin.

In an exemplary embodiment, a predetermined volume of an exemplary prepared cocktail, e.g., 50 μL, was added to each respective well in every 3 days intervals (in an overall duration of about 10 days). It may be understood that exemplary disclosed protocol as a whole, exemplary concentrations, volumes, time durations, etc. are not intended to be limiting.

Example 4: Screening Cultured Single Plasma Cells to Detect Single Plasma Cells Secreting Anti-Tetanus IgG Antibodies In this example, ELISA screening was performed to identify exemplary single plasma cells secreting IgG-type antibodies that may be capable of binding specifically to an exemplary tetanus toxoid. Ten days after culturing each respective single plasma cell in separate wells of an exemplary 96-well plate, an exemplary supernatant surrounding each respective plasma cell was withdrawn from each respective well and was added to a corresponding well in an exemplary 96-well microtiter plate (where each respective well was coated with an exemplary tetanus toxoid) to identify exemplary plasma cells secreting an exemplary anti-tetanus monoclonal antibody (IgG).

In an exemplary embodiment, a commercial humanized anti-tetanus IgG antibody was used as an exemplary positive control to obtain an exemplary standard curve. One or more exemplary microtiter plates were incubated at about 25° C. for about 60 min. Then, an exemplary supernatant was removed and each respective well was washed three times with an exemplary diluted washing solution comprising 1% BSA (bovine serum albumin) in PBS. Next, horse radish peroxidase (HRP)-conjugated anti-human IgG was added to each respective well and exemplary plates were incubated at about 25° C. for about 30 min. In an exemplary embodiment, an exemplary solution containing o-phenylenediamine and $H_2O_2$ was used as an exemplary substrate of HRP. Thereby, to accelerate substrate catalysis by HRP, exemplary plates containing o-phenylenediamine-$H_2O_2$ substrate were incubated at about 25° C. for 20 min. In an exemplary embodiment, enzyme-substrate reaction was terminated by adding 100 μL of an exemplary stop solution containing 0.5 M sulfuric acid to each respective well. Subsequently, absorbance (i.e., optical density (OD)) of exemplary samples in each respective well was measured at 450 nm. By performing an exemplary ELISA-screening method, one or more exemplary plasma cells were selected as candidates producing specific antibodies against tetanus toxoid. Exemplary selected plasma cells were used in further experiments to obtain mRNAs (messenger ribonucleic acid) encoding variable light (VL) and heavy (VH) chains of an exemplary anti-tetanus antibody.

Example 5: Obtaining VL and VH Gene Segments from Exemplary Selected Plasma Cells In this example, exemplary VL and VH gene segments (expressing VL and VH chains of an exemplary anti-tetanus antibody) were obtained from exemplary plasma cells' total RNA through extraction and reverse transcription polymerase chain reaction (RT-PCR). Thereby, total RNA of each selected plasma cells that may secrete an exemplary anti-tetanus antibody was extracted using a commercial cell lysis buffer. Then, using a cDNA (complementary deoxyribonucleic acid) synthesis kit, extracted RNA from each selected plasma cell was used as a template to synthesize cDNA. Briefly, an exemplary total RNA extracted from each selected plasma cell (set forth in Example 4) was reverse transcribed in a final volume of about 20 μL using 25 pmol of a random hexamer primer (provided in an exemplary commercial cDNA synthesis kit), 25 pmol oligo dT (deoxy Thymidine) primer, 1 μL of dNTP (deoxy nucleotide triphosphate) mix (10 μM), 20 units (U) of RNase inhibitor, and 200 U of prime-script reverse transcriptase. In an exemplary embodiment, an exemplary process of reverse transcription was carried out at 30° C. for a duration of 10 min, followed by raising the temperature to 42° C. for a duration of 1 h and 70° C. for a duration of 15 min.

An exemplary produced cDNA mixture was used as template for a first-round of PCR to obtain exemplary VH and VL chains of an exemplary anti-tetanus antibody using an exemplary immunoglobulin-specific primer set. For this purpose, 6 PCR sets were used, including: i) three sets for amplifying VH gene segment, and ii) three sets for amplifying VL kappa gene segment. In an exemplary embodiment, a second-round of an exemplary PCR reaction was conducted to add an exemplary linker sequence at exemplary 3' and 5' ends of exemplary amplified VH and VL segments, respectively, to obtain a final single-chain variable fragment (scFv). Table 1 below sets forth exemplary primers used throughout exemplary first and second rounds of an exemplary overlap extension PCR for amplifying exemplary VH and VL segments of anti-tetanus scFv, respectively. In further detail with respect to Table 1, exemplary nucleotides shown as "N" in exemplary primer sequences may include at least one of Adenosine, Thymidine, Uridine, Cytidine, Guanidine, and/or an exemplary modified nucleosides.

TABLE 1

Exemplary primers used throughout exemplary first and second rounds of an exemplary overlap extension PCR for amplifying exemplary VH and VL segments of anti-tetanus scFv, respectively, consistent with one or more exemplary embodiments of the present disclosure.

| Title | Sequence ID number | First/Second round | Forward/Reverse | Sequence (5' to 3') |
|---|---|---|---|---|
| 1VH1 | SEQ ID NO: 1 | First round | Forward | NAGGTGCAGCTGGTGCAGTCT |
| 1VH2 | SEQ ID NO: 2 | First round | Forward | CAGGTRCAGCTGCAGSAGTC |
| 1VH3 | SEQ ID NO: 3 | First round | Forward | GAGGTGCAGCTGNTGGAGTCT |
| 1Vk1 | SEQ ID NO: 4 | First round | Forward | GACATCSWGATGACCCAGTCTCC |

TABLE 1-continued

Exemplary primers used throughout exemplary first and second rounds of an exemplary overlap extension PCR for amplifying exemplary VH and VL segments of anti-tetanus scFv, respectively, consistent with one or more exemplary embodiments of the present disclosure.

| Title | Sequence ID number | First/ Second round | Forward/ Reverse | Sequence (5' to 3') |
|---|---|---|---|---|
| 1Vk2 | SEQ ID NO: 5 | First round | Forward | GATATTGTGATGACYCAGNCTCCACTCT |
| 1Vk3 | SEQ ID NO: 6 | First round | Forward | GAAATTGTNTGACNCAGTCTCCA |
| 1IgG | SEQ ID NO: 7 | First round | Reverse | GACSGATGGGCCCTTGGTGGA |
| 1Kc | SEQ ID NO: 8 | First round | Reverse | GAAGACAGATGGTGCAGCCACAGT |
| 2VH1 | SEQ ID NO: 9 | Second round | Forward | GAATAGGCCATGGCGNAGGTGCAGCTGGTGCAGTCT |
| 2VH2 | SEQ ID NO: 10 | Second round | Forward | GAATAGGCCATGGCGCAGGTRCAGCTGCAGSAGTC |
| 2VH3 | SEQ ID NO: 11 | Second round | Forward | GAATAGGCCATGGCGGAGGTGCAGCTGNTGGAGTCT |
| 2Vk1 | SEQ ID NO: 12 | Second round | Forward | TACAGGATCCACGCGTAGACATCSWGATGACCCAGTCTCC |
| 2Vk2 | SEQ ID NO: 13 | Second round | Forward | TACAGGATCCACGCGTAGATATTGTGATGACYCAGACTCCA |
| 2Vk3 | SEQ ID NO: 14 | Second round | Forward | TACAGGATCCACGCGTAGAAATTGTNNTGACACAGTCTCCA |
| 2IgG | SEQ ID NO: 15 | Second round | Reverse | CAGTCAAGCTTTGGGCCCTTGGTGGA |
| 2Kc | SEQ ID NO: 16 | Second round | Reverse | TGACAAGCTTGCGGCCGCGAAGACAGATGGTGCAGCCACAGT |

Each reaction of an exemplary first-round of PCR may include 2 μL of an exemplary synthesized cDNA as template, 400 nM of each primer, and 2×Taq polymerase master mix in a total volume of about 25 μL. In an exemplary embodiment, an exemplary thermal cycling program of each respective reaction may include 30 cycles, wherein each respective cycle includes 94° C. for a duration of 30 s, 62° C. for a duration of 30 s, and 72° C. for a duration of 30 s. In an exemplary embodiment, PCR products were diluted and used as template in an exemplary second-round of PCR. In particular, in a second round of PCR, exemplary concentrations of an exemplary reaction components and exemplary cycling conditions were identical to those of first round of PCR. The only exception was an exemplary annealing temperature, which was determined based on exemplary primers used in second round of PCR. Meanwhile, in an exemplary embodiment, an additional PCR was conducted on a non-immunoglobulin housekeeping gene as a quality control using hypoxanthine phosphoribosyl transferase (HPRT) specific primers (not disclosed herein).

Figure 3A:
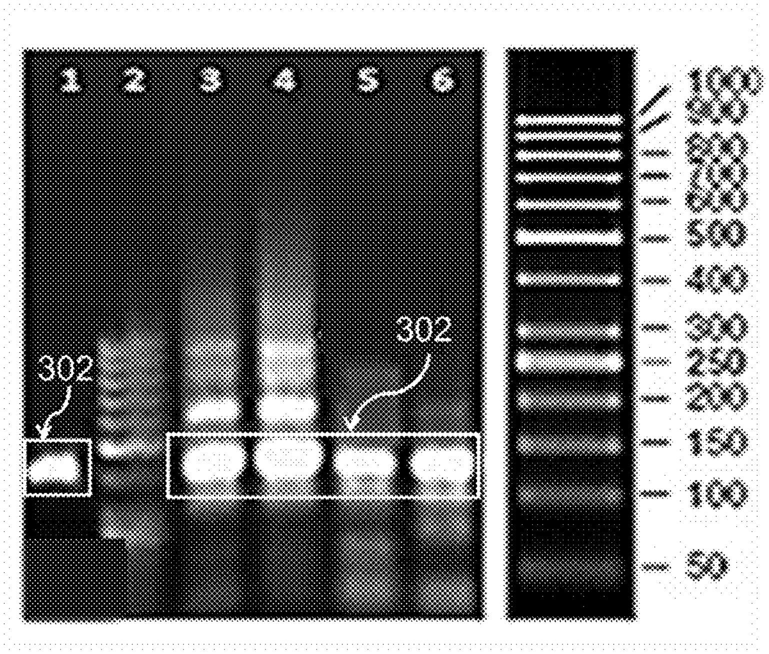
FIG. 3A illustrates an exemplary image of agarose gel electrophoresis of an exemplary first round of polymerase chain reaction (PCR) executed to amplify variable heavy (VH) segment of an exemplary anti-tetanus single-chain variable fragment (scFv), consistent with one or more exemplary embodiments of the present disclosure.
Figure 3B:
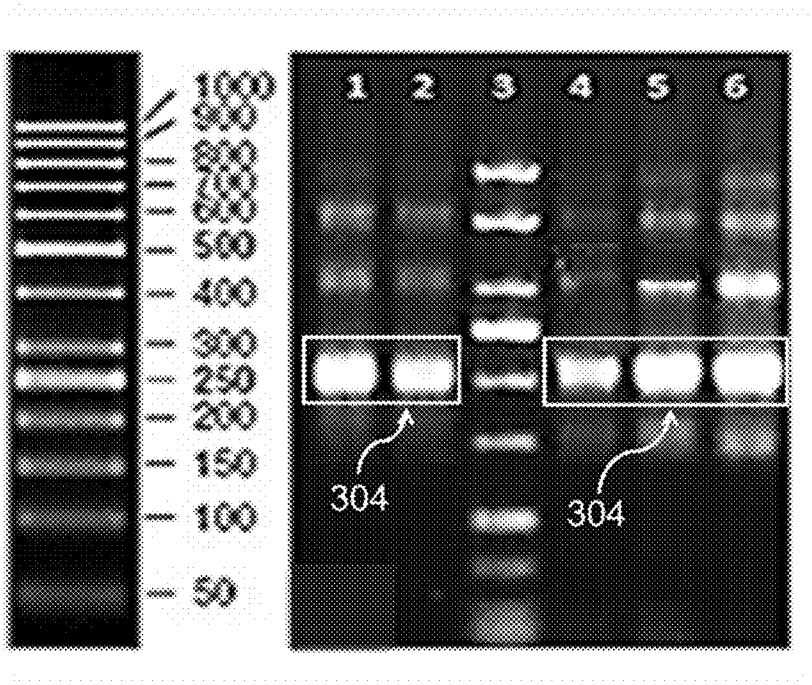
FIG. 3B illustrates an exemplary image of agarose gel electrophoresis of an exemplary second round of PCR executed to amplify variable light (VL) segment of an exemplary anti-tetanus scFv, consistent with one or more exemplary embodiments of the present disclosure.

In the next step, exemplary amplified PCR products were analyzed on 1% agarose gel and exemplary amplicons (i.e., VH and VL segments containing complementary regions of an exemplary linker sequence) were purified by gel purification. FIG. 3A illustrates image 300 of agarose gel electrophoresis of an exemplary first round of PCR executed to amplify VH segment of an exemplary anti-tetanus scFv, consistent with one or more exemplary embodiments of the present disclosure. In further detail with respect to image 300, Lane 2 is a 50 bp DNA marker/ladder and Lanes 1, 3, 4, 5 and 6 represent an exemplary amplified VH gene segments obtained from exemplary selected plasma cells in Example 4. As illustrated in image 300, an exemplary amplified VH segment (labeled as 302) was estimated to be about 400 bp in length. FIG. 3B illustrates image 303 of agarose gel electrophoresis of an exemplary second round of PCR executed to amplify VL segment of an exemplary anti-tetanus scFv, consistent with one or more exemplary embodiments of the present disclosure. In further detail with respect to image 303, Lane 3 represents a 50 bp DNA marker/ladder and Lanes 1, 2, 4, 5 and 6 represent exemplary amplified VL gene segments obtained from exemplary selected plasma cells set forth in Example 4. As illustrated in image 303, an exemplary amplified VH segment (labeled as 304) was estimated to be about 380 bp in length.

Figure 4:
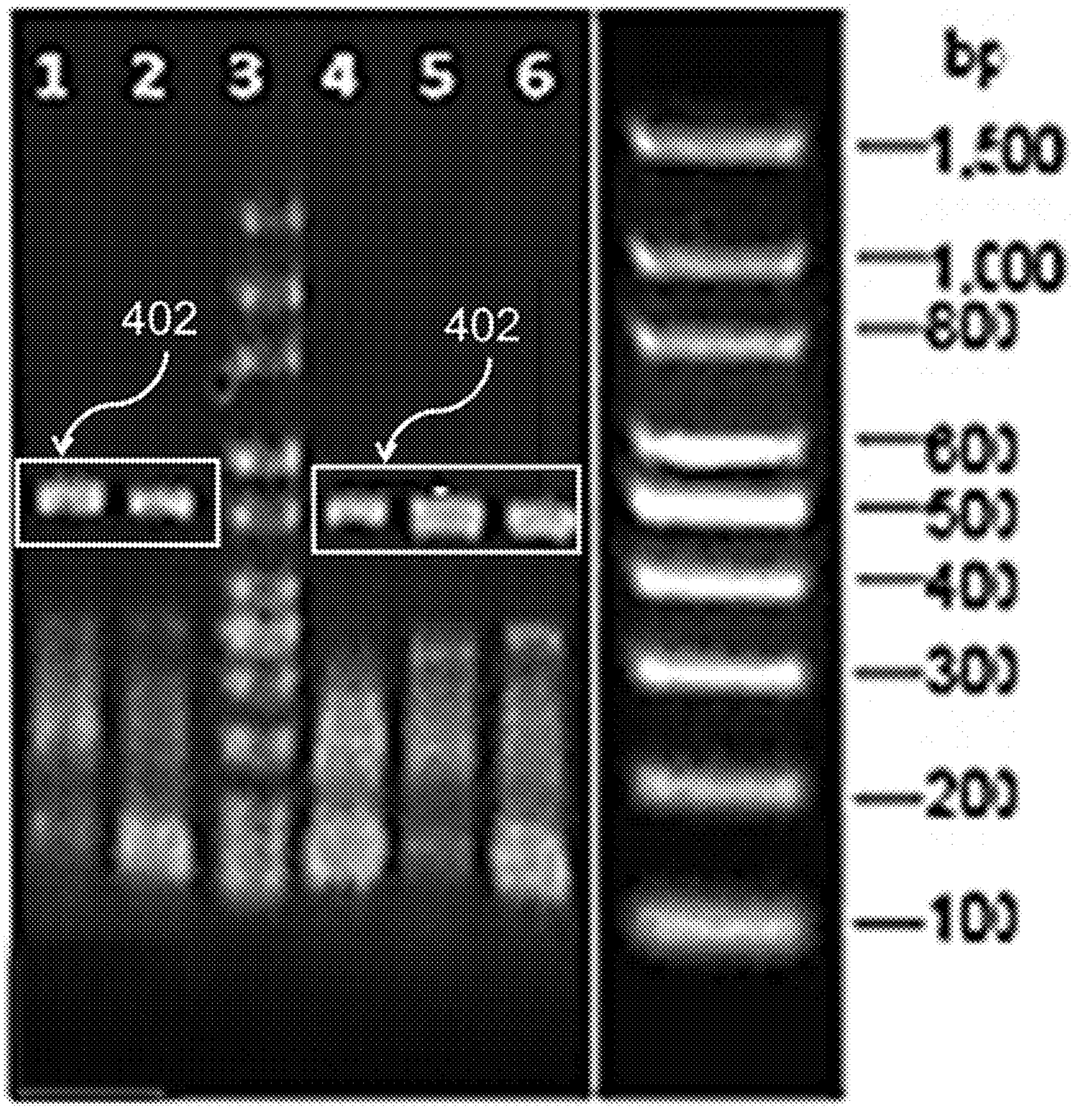
FIG. 4 illustrates an exemplary image of agarose gel electrophoresis of an exemplary overlap extension PCR executed to amplify an exemplary anti-tetanus scFv gene, consistent with one or more exemplary embodiments of the present disclosure.

In an exemplary embodiment, previously amplified VH and VL segments (serving as scFv components) were connected via an overlap extension PCR. An exemplary process of overlap extension PCR may utilize exemplary VH and VL PCR products, which had been purified through gel electrophoresis, as a template. In an exemplary embodiment, an exemplary reaction of overlap extension PCR was carried out under the following condition: 30 cycles of 95° C. for a duration of 30 s, 55° C. for a duration of 30 s, and 72° C. for a duration of 30 s. FIG. 4 illustrates image 400 of agarose gel electrophoresis of an exemplary overlap extension PCR executed to amplify an exemplary anti-tetanus scFv gene, consistent with one or more exemplary embodiments of the present disclosure. In further detail with respect to image 400, Lane 3 represents a 100 bp DNA marker/ladder and Lanes 1, 2, 4, 5 and 6 (labeled as 402) represent an exemplary anti-tetanus scFv gene that may be about 800 bp in size. In an exemplary embodiment, exemplary PCR products obtained from an exemplary overlap extension PCR were gel-purified and inserted into exemplary T-Vectors. "T-vector," also known as TA-Vector, may refer to a linearized plasmid capable of adding a Thymidine (T) overhang to match Adenosine (A) overhangs of a PCR product. In an exemplary embodiment, exemplary PCR fragments with an exemplary A overhang may be directly ligated to exemplary T-tailed plasmid vectors without further enzymatic treatment, except for the use of T4 DNA ligase.

Exemplary recombinant T-vectors were then transformed into DH5-alpha *E. coli* cells and further cultured in an exemplary bacterial culture medium comprising an exemplary antibiotic selected based on antibiotic-resistance gene of an exemplary T-Vector. Following cultivation of bacteria, a blue-white screening assay was conducted to identify positive recombinant clones that may harbor exemplary T-Vectors containing an exemplary ScFv gene. Exemplary recombinant T-vectors were subsequently purified for additional validation through DNA sequencing. In an exemplary embodiment, exemplary sequenced anti-tetanus scFv gene segments were further analyzed using exemplary open reading frame (ORF) finder tools to search for ORFs within exemplary scFv gene segments. Meanwhile, an exemplary sequence alignment software was used to analyze complementarity-determining regions (CDRs) of exemplary scFv sequences. Blast analysis revealed that an exemplary anti-tetanus scFv sequence may comprise exemplary VH and VL chains with about 86.4% and 97.64% identity to exemplary similar sequences found in an exemplary blast database, respectively. Meanwhile, an exemplary produced anti-tetanus scFv may have an exemplary nucleic acid sequence with at least 70% identity and/or similarity to an exemplary nucleic acid sequence set forth in Genbank accession number: 'MG725617.1'. In an exemplary embodiment, an exemplary anti-tetanus scFv may have a nucleic acid sequence with at least 80%, 81%, 82%, 83%, 84%, 85%, 86%, 87%, 88%, 89%, 90%, 91%, 92%, 93%, 94%, 95%, 96%, 97%, 98%, 99%, or 99.5% sequence identity to Genbank accession number: 'MG725617.1'.

Figure 5:
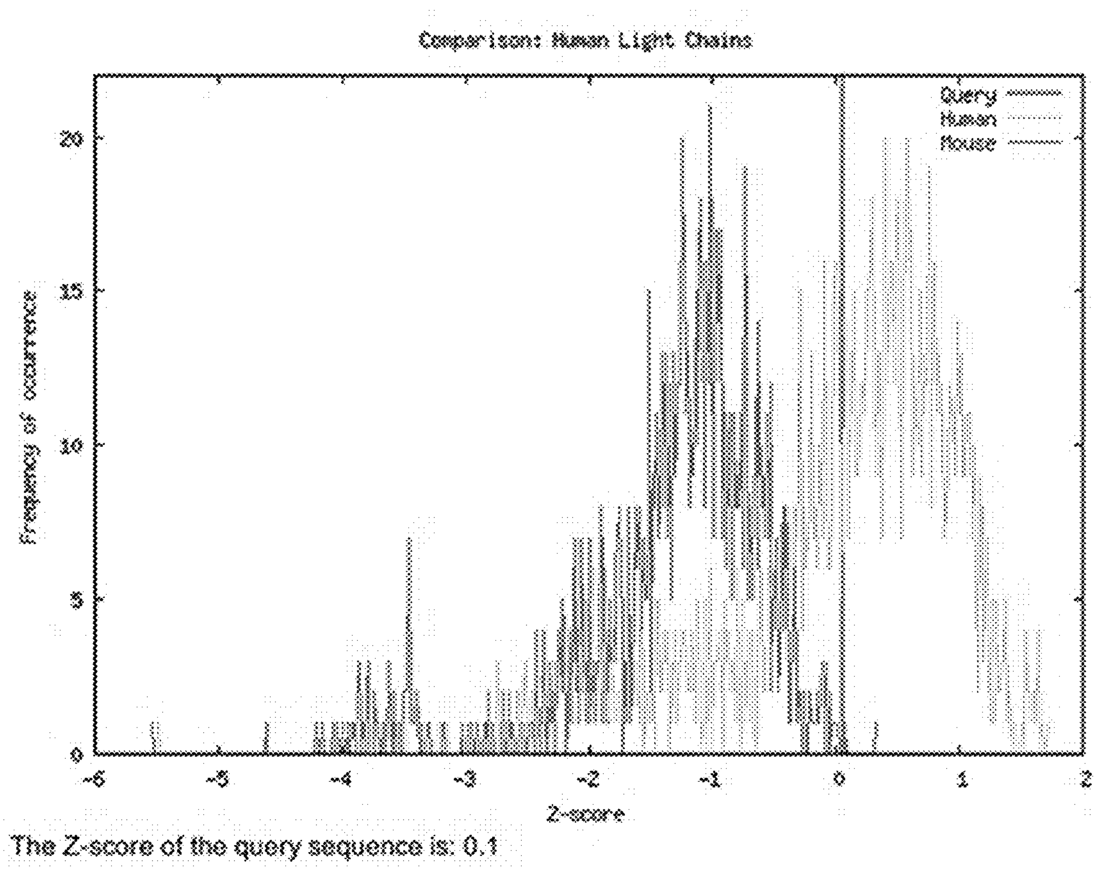
FIG. 5 shows an exemplary graph representing degree of humanness of anti-tetanus scFv, as determined by an exemplary obtained Z-score for kappa light chain of an exemplary scFv, consistent with one or more exemplary embodiments of the present disclosure.
Figure 6:
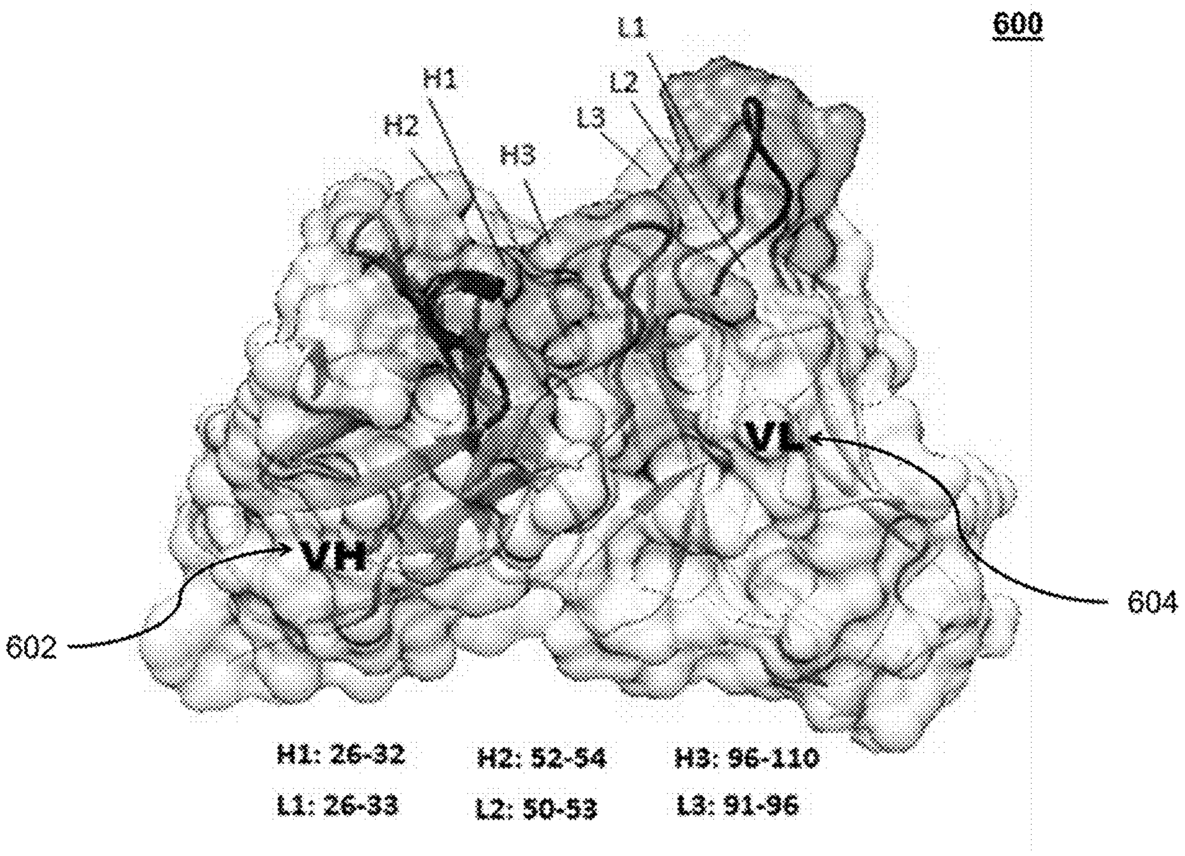
FIG. 6 illustrates an exemplary image representing 3D structure of an exemplary anti-tetanus scFv, consistent with exemplary embodiments of the present disclosure.

Humanness and Z-score of an exemplary anti-tetanus scFv sequences were evaluated using an exemplary antibody research database. FIG. 5 shows graph 500 representing degree of humanness of anti-tetanus scFv, as determined by an exemplary obtained Z-score for kappa light chain of an exemplary scFv, consistent with one or more exemplary embodiments of the present disclosure. In further detail with respect to graph 500, an exemplary anti-tetanus scFv achieved a significantly high humanness score. Three-dimensional (3D) structure modeling of an exemplary scFv was accomplished using an exemplary web server for automatic modelling of immunoglobulin variable domains. FIG. 6 illustrates image 600 representing 3D structure of an exemplary anti-tetanus scFv, consistent with exemplary embodiments of the present disclosure. as illustrated in image 600, exemplary VH and VL chains of an exemplary scFv are labeled as 602 and 604, respectively, and exemplary CDRs of an exemplary scFV are labeled as H1, H2, H3, L1, L2, and L3.

Example 6: Bacterial Expression of Anti-Tetanus scFv

Figure 7:
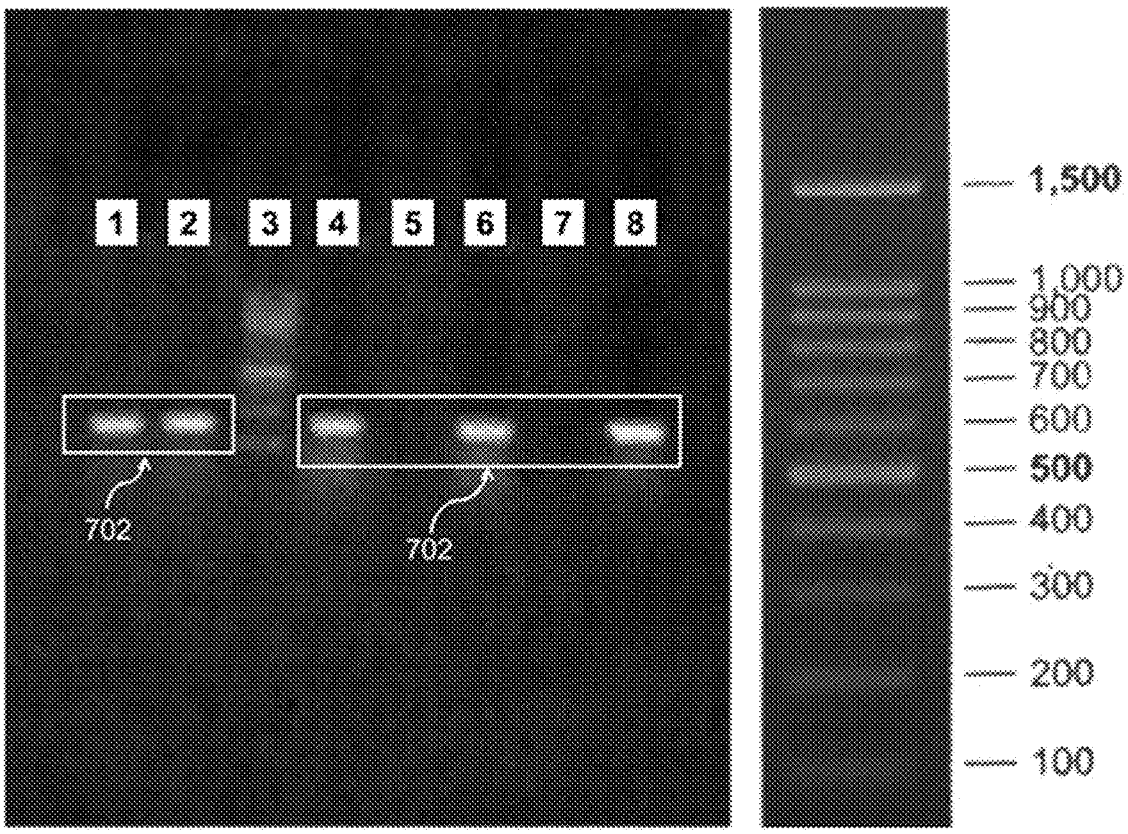
FIG. 7 shows an exemplary image which depicts agarose gel electrophoresis results obtained from an exemplary colony PCR performed on exemplary cultivated colonies post-transformation of an exemplary pET28 bearing an exemplary anti-tetanus scFV, consistent with one or more exemplary embodiments of the present disclosure.

This example describes transformation and expression of an exemplary anti-tetanus scFv gene (that was cloned into an exemplary T-vector as explained in Example 5) in a bacterial host, such as *E. coli*. For this purpose, after sequencing and ORF analysis of an exemplary scFv gene, an exemplary fragment of an exemplary scFv was selected to be transformed into *E. coli* BL21. An exemplary selected scFv gene was cleaved using two exemplary restriction endonucleases that their recognition sites were previously added into an exemplary reverse primer 2IgG and exemplary forward primers set forth as VH1, VH2, and VH3 as in Table 1. An exemplary cleaved scFv gene was inserted/subcloned into an exemplary pET28 expression vector and further transformed into *E. coli* BL21 competent cells by heat shock transformation method. Then, an exemplary transformed bacteria was cultured in an exemplary medium containing an exemplary antibiotic (selected based on an exemplary antibiotic-resistance gene incorporated in an exemplary pET28 vector). Next, exemplary colonies that have been cultivated on an exemplary culture medium, such as Luria-Bertani (LB) agar, were evaluated by colony PCR to identify exemplary colonies harboring an exemplary recombinant pET28 vector. FIG. 7 shows image 700 which depicts agarose gel electrophoresis results obtained from an exemplary colony PCR performed on exemplary cultivated colonies post-transformation of an exemplary pET28 bearing an exemplary anti-tetanus scFV, consistent with one or more exemplary embodiments of the present disclosure. The colony PCR that was conducted successfully amplified the scFv gene in the positive colonies. In further detail with respect to FIG. 7, an exemplary PCR product of 400 bp, labeled as 702, was observed in Lanes 1, 2, 4, 6 and 8 (exemplary PCR product 702 may be an exemplary amplification product of an exemplary scFv gene). Lane 3 illustrated in image 700 may contain an exemplary DNA marker/ladder of 100 bp. As illustrated in image 700, an exemplary colony PCR resulted in amplification of an exemplary scFv gene in exemplary positive colonies. A 400 bp PCR product (labeled as 702) was found in Lanes 1, 2, 4, 6 and 8 shown in image 700 that may be an exemplary amplification product of an exemplary scFv gene. Additionally, Lane 3 displays an exemplary DNA marker/ladder of 100 bp.

In an exemplary embodiment, one or more exemplary colonies selected based on an exemplary colony PCR were further inoculated into 6 mL of LB medium containing Kanamycin and were incubated overnight (e.g., 8-16 hours) at 250 rpm in a shaking incubator at 37° C., until reaching an $OD_{600}$ of 0.6. To induce protein expression in an exemplary transformed *E. coli* BL21 bacteria, IPTG (Isopropyl β-d-1-thiogalactopyranoside) with a final concentration of 0.8 mM was added into an exemplary culture media and incubated for 4 hours at about 37° C. Exemplary bacterial cell pellets were analyzed for protein expression using a 12% sodium dodecyl sulphate-polyacrylamide gel electrophoresis (SDS-PAGE) before and after IPTG addition.

Figure 8:
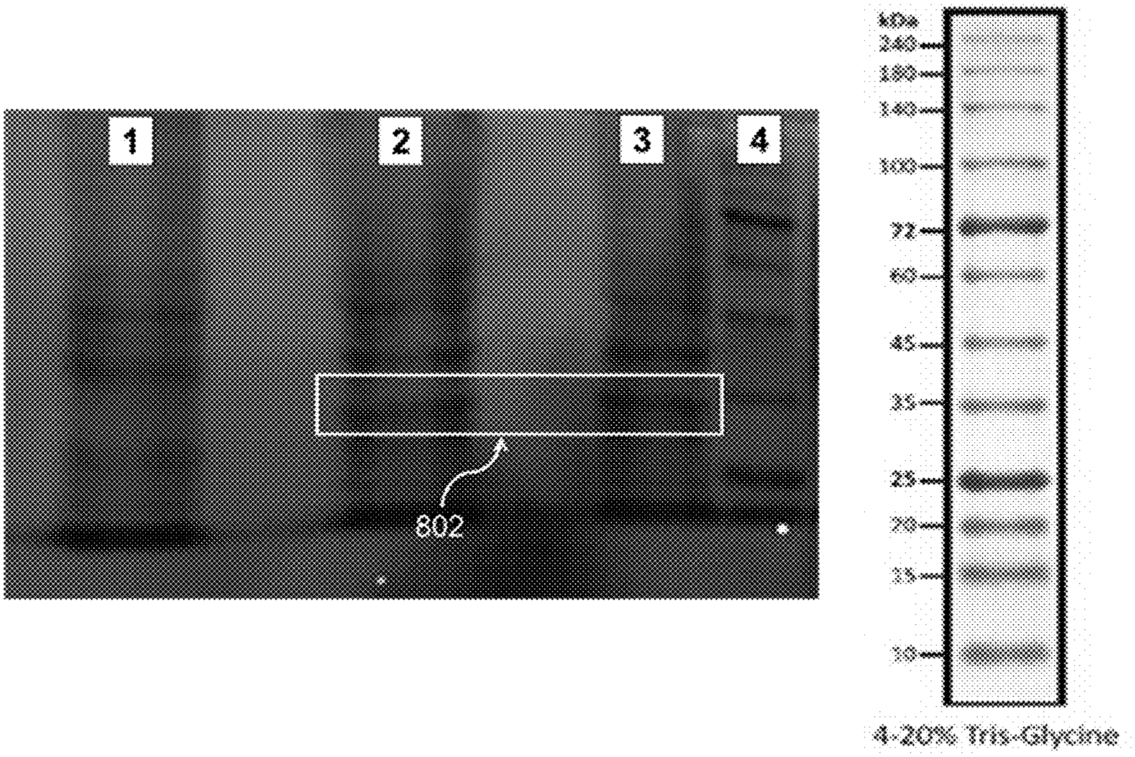
FIG. 8 illustrates an exemplary image representing sodium dodecyl sulphate-polyacrylamide gel electrophoresis (SDS-PAGE) analysis of an exemplary transformed *Escherichia coli* (*E. coli*) BL21 before and after protein expression induction by an inducer, e.g., Isopropyl β-d-1-thiogalactopyranoside (IPTG), consistent with one or more exemplary embodiments of the present disclosure.

To analyze the bacterial pellets by SDS-PAGE, culture samples were collected at different points, such as before IPTG addition (TO) and during incubation in IPTG (T3 and T4). Exemplary samples were pelleted by centrifuging at 9000 rpm for 3 min followed by suspending exemplary pellets in an exemplary SDS-PAGE sample buffer containing 1% SDS and 10 mM DTT (dithiothreitol). Exemplary suspended pellets were boiled for 5 min. Then, 5 μL of each respective sample was loaded on an exemplary 12% SDS-PAGE. Exemplary protein bands were visualized by performing a conventional procedure of staining and distaining. FIG. 8 illustrates image 800 representing SDS-PAGE analysis of an exemplary transformed *E. coli* BL21 before and after protein expression induction by an inducer, e.g., IPTG, consistent with one or more exemplary embodiments of the present disclosure. In further detail with respect to image 800, Lane 1, 2 and 3 were respectively loaded with exemplary bacterial lysate samples collected before IPTG induction, following 3 hours of IPTG induction, and following 4 hours of IPTG induction. As illustrated in image 800, protein band 802 with molecular weight of 35 KD, corresponding to an exemplary anti-scFv protein, was detected in exemplary bacterial lysates that were collected after 3 and 4 hours of IPTG induction.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. An element proceeded by “a” or “an” does not, without further constraints, preclude the existence of additional identical elements in the process, method, article, or apparatus that comprises the element.

Unless otherwise stated, all measurements, values, ratings, positions, magnitudes, sizes, and other specifications that are set forth in this specification, are approximate, not exact. They are intended to have a reasonable range that is consistent with the functions to which they relate and with what is customary in the art to which they pertain.

It will be understood that the terms and expressions used herein have the ordinary meaning as is accorded to such terms and expressions with respect to their corresponding respective areas of inquiry and study, except where specific meanings have otherwise been set forth herein. Relational terms such as “first” and “second” and the like may be used solely to distinguish one entity or action from another without necessarily requiring or implying any actual such relationship or order between such entities or actions.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter. While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for producing an antibody fragment, the method comprising:

obtaining a plurality of plasma cells;

preparing a plurality of modified cell culture substrates, wherein preparing each modified cell culture substrate of the plurality of modified cell culture substrates comprises:

culturing a plurality of HS-5 cells on each cell culture substrate of a plurality of cell culture substrates at a temperature level between 36° C. and 37° C. until a confluency of the plurality of HS-5 cells reaches 70-90%; and incubating the cultured plurality of HS-5 cells in 3 ng/ml colchicine at a temperature level between 36° C. and 37° C. for a time duration between 18 and 24 hours;

seeding each plasma cell of the plurality of plasma cells on the each modified cell culture substrate of the plurality of modified cell culture substrates;

forming a plurality of cultured single plasma cells by culturing each seeded plasma cell in a culture medium at a temperature level between 36° C. and 37° C. for a time duration of at least 10 days, the culture medium comprising a conditioned medium harvested from a culture of HS-5 cells, Insulin with a concentration of 10 mg/mL, Transferrin with a concentration of 5.5 mg/mL, Selenium with a concentration of 6.8 μg/mL, and Pyruvate with a concentration of 1 mM;

selecting one or more single plasma cells that secrete an antibody from among the plurality of cultured single plasma cells, the antibody comprising a full-length antibody with a Variable Light (VL) chain and a Variable Heavy (VH) chain;

obtaining one or more nucleic acid sequences encoding the VL chain and the VH chain of the antibody from the one or more single plasma cells that secrete the antibody;

assembling the one or more nucleic acid sequences into a nucleic acid construct, thus encoding the antibody fragment comprising at least one of the VL chain and the VH chain;

forming a recombinant vector by cloning the nucleic acid construct encoding the antibody fragment into a vector;

transferring the recombinant vector to a host cell; and expressing the antibody fragment in the host cell.

2. A method of producing a nucleic acid construct encoding an antibody fragment, the method comprising:

obtaining a plurality of plasma cells;

preparing a plurality of modified cell culture substrates, wherein preparing each modified cell culture substrate of the plurality of modified cell culture substrates comprises:

culturing a plurality of human bone marrow stomal cells (h-BMSCs) on each cell culture substrate of a plurality of cell culture substrates until a confluency of the plurality of h-BMSCs reaches to at least 70%; and incubating the cultured plurality of h-BMSCs in 2.7-3.3 ng/ml colchicine at a temperature level between 36° C. and 37° C. for a time duration between 18 and 24 hours;

seeding each plasma cell of the plurality of plasma cells on the each modified cell culture substrate of the plurality of modified cell culture substrates;

forming a plurality of cultured single plasma cells by culturing each seeded plasma cell in a culture medium for a time duration of at least 10 days, the culture medium comprising a conditioned medium harvested from a culture of h-BMSCs, Insulin with a concentration of 9.5-10.5 mg/mL, Transferrin with a concentration of 5-6 mg/mL, Selenium with a concentration of 6-7.5 μg/mL, and Pyruvate with a concentration of 0.7-1.3 mM;

selecting one or more single plasma cells that secrete an antibody from among the plurality of cultured single plasma cells;

obtaining one or more nucleic acid sequences encoding a Variable Light (VL) chain and a Variable Heavy (VH) chain of the antibody from the one or more single plasma cells that secrete the antibody; and assembling the one or more nucleic acid sequences into a nucleic acid construct, thus encoding the antibody fragment comprising at least one of the VL chain and the VH chain.

3. The method of claim 2, wherein the h-BMSCs comprise HS-5 cells.

4. The method of claim 2, wherein the conditioned medium harvested from the culture of h-BMSCs comprises Roswell Park Memorial Institute (RPMI) medium.

5. The method of claim 2, wherein culturing the plurality of h-BMSCs on the each cell culture substrate of the plurality of cell culture substrates until the confluency of the plurality of h-BMSCs reaches to at least 70% comprises culturing a plurality of HS-5 cells on the each cell culture substrate of the plurality of cell culture substrates at a temperature level between 36° C. and 37° C. until a confluency of the plurality of HS-5 cells reaches to 70-90%.

6. The method of claim 2, wherein incubating the cultured plurality of h-BMSCs in 2.7-3.3 ng/ml colchicine at the temperature level between 36° C. and 37° C. for the time duration between 18 and 24 hours comprises incubating the cultured plurality of h-BMSCs in 3 ng/ml colchicine at a temperature level between 36° C. and 37° C. for a time duration between 18 and 24 hours.

7. The method of claim 2, wherein culturing the each seeded plasma cell in the culture medium for the time duration of at least 10 days comprises culturing the each seeded plasma cell in the culture medium at a temperature level between 36° C. and 37° C. for a time duration of at least 10 days.

8. The method of claim 7, wherein the culture medium comprises a conditioned medium harvested from a culture of HS-5 cells, Insulin with a concentration of 10 mg/mL, Transferrin with a concentration of 5.5 mg/mL, Selenium with a concentration of 6.8 μg/mL, and Pyruvate with a concentration of 1 mM.

9. The method of claim 2, wherein selecting the one or more single plasma cells that secrete the antibody from among the plurality of cultured single plasma cells comprises selecting the one or more single plasma cells that secrete the antibody from among the plurality of cultured single plasma cells by performing an enzyme-linked immunosorbent assay (ELISA) on supernatants collected from the plurality of cultured single plasma cells.

10. The method of claim 9, wherein selecting the one or more single plasma cells that secrete the antibody from among the plurality of cultured single plasma cells by performing the ELISA comprises selecting the one or more single plasma cells that secrete the antibody from among the plurality of cultured single plasma cells by the ELISA, the ELISA comprising coating a substrate with a target antigen and detecting binding of the antibody secreted by the one or more single plasma cells to the target antigen.

11. The method of claim 2, further comprising:

forming a recombinant vector by cloning the nucleic acid construct encoding the antibody fragment into a vector;

transferring the recombinant vector to a host cell; and expressing the antibody fragment in the host cell.

12. The method of claim 2, wherein the one or more nucleic acid sequences encoding the VL chain and the VH chain comprise one or more messenger Ribonucleic Acid (mRNA).

13. The method of claim 2, wherein the one or more nucleic acid sequences encoding the VL chain and the VH chain comprise one or more complementary Deoxyribonucleic Acid (cDNA).

14. The method of claim 2, wherein obtaining the one or more nucleic acid sequences encoding the VL chain and the VH chain of the antibody from the one or more single plasma cells comprises:

extracting a total RNA of the one or more single plasma cells that secrete the antibody, wherein the total RNA of the one or more single plasma cells comprises the one or more nucleic acid sequences; and amplifying the one or more nucleic acid sequences encoding the VL chain and the VH chain of the antibody.

* * * * *